United States Patent [19]

Willard et al.

[11] Patent Number: 5,577,410
[45] Date of Patent: Nov. 26, 1996

[54] METHOD AND APPARATUS FOR TESTING SNACK PRODUCT INGREDIENTS

[75] Inventors: Miles J. Willard, 154 E. 49th South, Idaho Falls, Id. 83404; Kyle E. Dayley; LaRue Remer, both of Rigby, Id.; Jane Arnold, Idaho Falls, Id.

[73] Assignee: Miles J. Willard, Idaho Falls, Id.

[21] Appl. No.: 199,825

[22] Filed: Feb. 22, 1994

[51] Int. Cl.$^6$ .................................................. G01N 33/10
[52] U.S. Cl. ............................ 73/169; 426/231; 426/233; 426/496
[58] Field of Search ................................ 73/169, 864.41; 426/231, 233, 496, 499, 539

[56] References Cited

U.S. PATENT DOCUMENTS

| | | | |
|---|---|---|---|
| 2,275,341 | 3/1942 | Brabender | 265/16 |
| 3,169,395 | 2/1965 | Enoch et al. | 73/169 |
| 3,463,014 | 8/1969 | Katz et al. | 73/432 |
| 3,533,801 | 10/1970 | Wenger | 426/499 X |
| 3,711,296 | 1/1973 | La Warre, Sr. | 426/499 |
| 3,788,139 | 1/1974 | Rubio et al. | 73/169 |
| 3,789,660 | 2/1974 | Rubio et al. | 73/169 |
| 3,886,291 | 5/1975 | Willard | 426/637 |
| 3,966,990 | 6/1976 | Cremer et al. | 426/496 X |
| 3,989,858 | 11/1976 | Williams | 426/496 X |
| 3,998,975 | 12/1976 | Liepa | 426/550 |
| 4,262,024 | 4/1981 | Mathason | 426/231 |
| 4,640,843 | 2/1987 | Matuszak et al. | 426/626 |
| 4,680,181 | 7/1987 | Budd et al. | 426/439 |
| 4,766,766 | 8/1988 | Ahlert et al. | 73/169 |
| 4,838,081 | 6/1989 | Finley et al. | 73/169 |
| 4,931,303 | 6/1990 | Holm et al. | 426/549 |
| 4,973,481 | 11/1990 | Hunt et al. | 426/144 |
| 5,100,686 | 3/1992 | Hunt et al. | 426/549 |
| 5,104,673 | 4/1992 | Fazzolare et al. | 426/549 |
| 5,192,574 | 3/1993 | Hunt et al. | 426/549 |
| 5,314,650 | 5/1994 | Adler et al. | 423/461 X |

FOREIGN PATENT DOCUMENTS

| | | | |
|---|---|---|---|
| 0186245 | 12/1985 | European Pat. Off. | A23L 1/164 |
| 2368706 | 10/1976 | France | G01N 11/04 |
| 1101021 | 11/1961 | Germany . | |
| 61-209337 | 9/1986 | Japan | G01N 11/14 |
| 441373 | 12/1974 | U.S.S.R. . | |

*Primary Examiner*—Christopher W. Fulton
*Assistant Examiner*—Willie Morris Worth
*Attorney, Agent, or Firm*—Hopkins, Roden, Crockett, Hansen & Hoopes

[57] ABSTRACT

A method for testing the ingredients of fabricated snack products includes the steps of; producing snack product test pieces using a test ingredient; evaluating certain characteristics of the test pieces; and then using this information to predict the characteristics of a fabricated snack product containing the test ingredient. Initially, a dough containing the test ingredient is mixed under controlled conditions. A quantity of the dough is extruded using an extrusion apparatus adapted to extrude the dough at a uniform rate regardless of the dough's consistency. The extruded dough is then cut into dough pieces having a uniform length, wall thickness and density. Next, the dough pieces are cooked at a predetermined temperature for a predetermined time to form the snack product test pieces. Characteristics of the test pieces are determined and analyzed as a predictor of similar characteristics in a fabricated snack product containing the test ingredient.

21 Claims, 12 Drawing Sheets

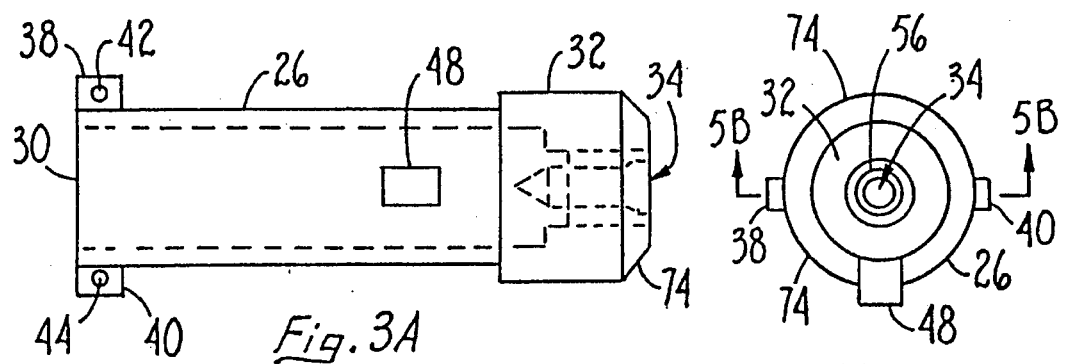
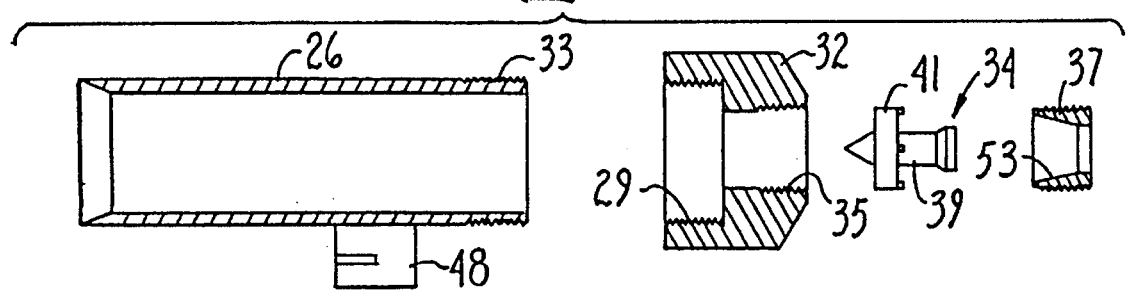
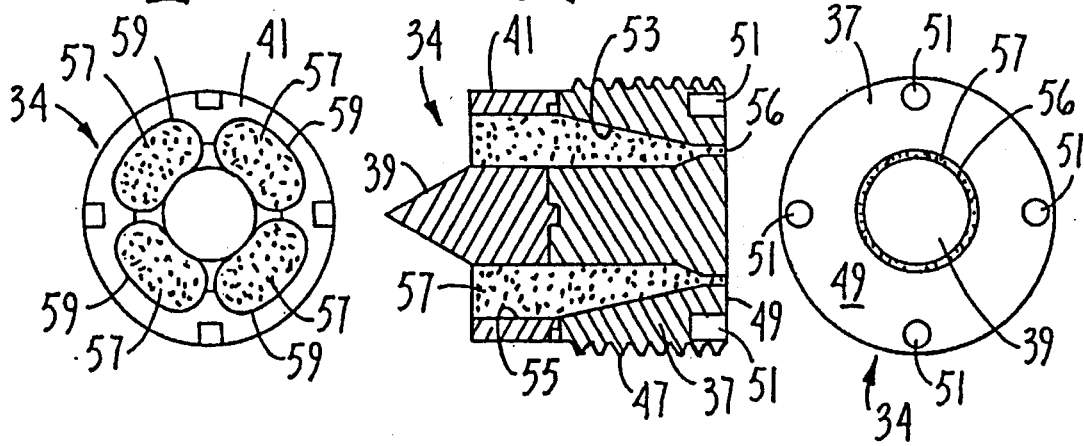

5,577,410

METHOD AND APPARATUS FOR TESTING SNACK PRODUCT INGREDIENTS

FIELD OF THE INVENTION

The present invention relates to testing procedures for food products. More specifically this invention relates to a method and apparatus for testing the ingredients for fabricated snack food products.

BACKGROUND OF THE INVENTION

Fabricated snack products are popular with consumers throughout the world. Fabricated snack products are made from potato, corn, and a variety of cereal grains. Exemplary snack products include Ripplins™ brand potato snacks manufactured by the Keebler Co., Pringles™ brand potato snacks manufactured by the Proctor & Gamble Co. and Doritos™ brand tortilla chips manufactured by Frito-Lay.

These snack products are typically fabricated from some type of dough. The dough usually contains a primary ingredient, such as potato, corn, or cereal based solids, mixed with or containing water, spices and various other dry ingredients. The dry ingredients may include starches in powder, granular, or flake form, added as a binder for the dough, or to produce a certain texture or expansion in the cooked snack product. By way of example, a basic formula for a fabricated potato snack includes: potato flakes, raw potato starch, ground dehydrated potatoes, sugar, salt and various flavoring ingredients.

During a testing process, the dough ingredients are mixed in predetermined quantities, under controlled conditions, to form a batch of dough having a desired moisture content and consistency. The dough is then formed into a desired shape (e.g. chips, rings) prior to cooking. Cooking may be by frying or baking at a predetermined temperature for a predetermined time. Forming of the individual dough pieces may be accomplished using a piston extrusion apparatus that forces the dough through a die. Alternately, the dough can be sheeted to a predetermined thickness and then cut into uniform small pieces having a desired shape. Piston extrusion is preferred, however, because it provides more consistent control in the forming of the test product.

One goal of any process for making fabricated snacks is to be able to consistently produce certain important characteristics in the snack product which affect the quality of the snack product and its success in the market. Such important characteristics of a snack product include flavor, color, thickness, moisture content, texture, fat content and degree of bubbling.

Some characteristics of a snack product are intended to achieve a certain perception by the consumer. As an example, the internal expansion of a snack product influences the texture, mouth feel, and crispness of the product. A product, such as a fabricated potato snack, which is intended to be crisp like a conventional potato chip, must therefore be expanded to the same degree.

Expansion occurs during the frying or baking process as the water present in the snack dough escapes from the formed dough pieces. The expansion of the snack product is often expressed as the ratio of the snack thickness to the original dough thickness. Expansion during frying is a function of the quantity and type of the internal bubbling that occurs during the frying or baking process, which in turn is a function of many factors including, for example, the moisture and free gelatinized starch content of the snack dough. For baked products, leavening systems and baking conditions are used to achieve a desired expansion.

Many characteristics of a snack product can be measured directly, such as thickness, moisture content, color and fat content. Other characteristics, such as texture, flavor and bubble content, require a more subjective system of evaluation. In this regard, various rating and evaluation techniques have been developed in the art to quantify important characteristics of fabricated snack products. U.S. Pat. No. 4,931,303 to Holm et al., which is incorporated herein by reference, describes an exemplary system for evaluating the bubble size and bubble distribution in a fried snack product.

Different methods have also been developed for evaluating doughs used to make snack products. The previously cited patent to Holm et al. describes a rating system for evaluating the consistency of a snack product dough. Under this rating system, various visual and manual characteristics are used to quantify a dough's consistency. A dough receives a rating from Type 1 to Type 9. A Type 1 dough has a dry/friable consistency and can be squeezed into a ball by hand only with difficulty. A Type 9 dough has a sticky/adhesive consistency and is similar to bread dough. Various intermediate doughs (e.g., Types 2–8) have other characteristic consistencies as shown as follows.

1. Dry, friable, powdery dough—can be squeezed by hand into a ball only with difficulty.
2. Dry, friable—more easily squeezed into a ball.
3. Easily squeezed into a ball which breaks apart when dropped.
4. Friable—some small agglomerates remain after mixing.
5. Borderline friable/cohesive, discharged with ease from mixer—many random agglomerates after mixing. Hand-formed ball does not break easily when dropped.
6. Predominantly agglomerates easily molded into ball which feels wet—discharged from mixer with difficulty.
7. All large agglomerates—discharged with difficulty from mixer. Hand-formed ball does not break when dropped.
8. Completely uniform, cohesive mixture—discharged from mixer as a single non-adhesive dough.
9. Uniform adhesive dough similar to bread dough—cannot be discharged from mixer except as single unit which sticks to fingers.

In general, the different methods for evaluating a snack product developed in the industry thus far have been directed to evaluating either the characteristics of the fabricated snack product or the dough used to make the snack product. These characteristics, however, are dependent on the properties of the individual ingredients which make up the snack product or dough.

As an example, raw or pregelatinized starches used in the formulation of snack products may have different properties which will affect the characteristics of the snack product. Specifically, starches that vary in water absorption, gelatinization temperature or degree of retrogradation will cause structural variations in snack products which contain the starch ingredients. To date, however, no test has been developed that is effective in predicting the performance of a particular starch as an ingredient in a snack product.

The free gelatinized starch content of a snack ingredient may also affect the characteristics of the finished snack product. The texture of fried fabricated potato snack products is particularly affected by the free gelatinized starch content. One widely used grading system for potato solids, known as the "iodine index", measures the "free soluble starch" contained in potato flakes. As disclosed in U.S. Pat. No. 3,998,975 to Liepa, the iodine index may be useful in some applications for predicting dough formulations for sheeted potato-based snack products. This index, however, has not proven to be a reliable method for predicting important characteristics of a finished snack product. In addition, its use is mainly limited to potato snacks.

In light of this, it would be desirable to have a reliable method for evaluating the functional properties of the ingredients which are used in fabricating snack products. This evaluation could then be used to predict the performance of the different ingredients of a fabricated snack product and the characteristics of the finished product.

This need is compounded by the lack of equipment in the snack industry suitable for reproducing fabricated snack products in the laboratory. In particular, small scale extrusion apparatus suitable for consistently extruding dough pieces for cooking are generally not available. In the past, laboratory extrusion apparatus has typically been of a makeshift nature. A modified pasta press, for example, may sometimes be used in a laboratory setting for extruding small batches of dough. Such makeshift extrusion apparatus, however, cannot efficiently extrude a snack food dough over a range of dough consistencies. This is a problem because one test ingredient may produce a soft, flowable dough, whereas another test ingredient may produce a firm, non-flowable dough.

The uniformity of the extruded dough is also a problem. Most extrusion apparatus typically depend on a pressure driven piston to force the dough through a die orifice. With a pressure driven piston, the pressure and flow rate generated during the extrusion process vary as a function of a dough's consistency. A dough with a Type 1 consistency will require more pressure to extrude than a dough with a Type 6 consistency. At the same extrusion pressure, the rate of extrusion will vary markedly with different dough consistencies.

Furthermore, a dough under test may not have a perfectly uniform consistency. This will cause the extrusion pressure and the rate of extrusion to fluctuate. The characteristics of the extruded dough pieces (e.g. density, texture, thickness) will thus not be uniform. In order to provide reliable comparisons between different snack product dough pieces, however, an extrusion apparatus must produce a substantially uniform extrudate from a dough, regardless of the consistency of the dough. In general, a laboratory sized extrusion apparatus, suitable for extruding uniform dough pieces over a range of dough consistencies is not available.

In view of these and other problems, there is a need in the art for reliable methods and apparatus for testing and evaluating the ingredients used in fabricated snack products. Accordingly, it is an object of the present invention to provide a method and apparatus for testing and evaluating ingredients for fabricated snack products.

It is a further object of the present invention to provide a method for testing and evaluating ingredients for snack products, that is simple, reliable, and in which process parameters can be precisely controlled during the formation of snack product test pieces.

It is yet another object of the present invention to provide a laboratory extrusion apparatus suitable for extruding and cutting snack product dough pieces having a uniform size and shape that permits testing and precise evaluation of individual ingredients.

It is a further object of the present invention to provide a laboratory extrusion apparatus for extruding substantially uniform snack dough pieces from small batches of dough at a constant rate, regardless of the dough's consistency, and immediately frying the dough pieces for evaluation.

SUMMARY OF THE INVENTION

In accordance with the present invention, a novel method and apparatus for testing and evaluating ingredients for fabricated snack products are provided. The method of the invention includes the steps of: producing snack product test pieces incorporating a test ingredient, determining and evaluating certain characteristics of the test pieces, and, then predicting similar characteristics in a fabricated snack product which contains the test ingredient.

As a first step, a dough containing the test ingredient and a predetermined quantity of water are mixed under controlled conditions. The dough is then extruded at a uniform rate into a predetermined shape and cut into dough pieces each having the same length. Next, the dough pieces are cooked, preferably by frying, to form cooked test pieces. Characteristics or attributes of the cooked test pieces, such as expansion, color, weight, texture, thickness, fat content, flavor, and others, are then determined. This provides information for evaluating the test ingredient and for predicting the performance of the test ingredient in a fabricated snack product.

The test pieces may be evaluated by comparison to a control piece fabricated in the same manner with an ingredient having known properties. This provides a benchmark for evaluating the test ingredients. The test pieces may also be evaluated by comparison to other test pieces fabricated in the same manner using different test ingredients. Furthermore, evaluation may be by combining the test ingredient with another ingredient having known characteristics, and then noting the suitability of the test ingredient for a fabricated snack product. Finally, evaluation may be a simple assessment of the suitability of the characteristics of a test ingredient for a fabricated snack product.

An extrusion apparatus constructed in accordance with the invention is adapted to produce cut dough pieces, each of which has a same length and a uniform density. Differences in the cooked test pieces can thus be attributable to the raw materials used, specifically the test ingredient, and not to the testing process.

The extrusion apparatus, broadly stated, includes a support frame, an extrusion tube and extrusion piston for extruding the dough at a uniform rate of extrusion to form an extrudate having a uniform density, and a cutter assembly for cutting the extrudate into dough pieces of the same length. The extrusion tube is detachably mounted to the support frame. The extrusion tube includes an inlet end that is open for receiving a quantity of the dough. The extrusion tube also includes an outlet end with a removable extrusion die. The extrusion die is formed with an annular orifice for forming the dough into a continuous hollow cylinder of extrudate.

The extrusion piston is reciprocally mounted within the extrusion tube. The extrusion piston forces the dough through the annular orifice of the extrusion die using mechanical pressure. The extrusion piston is driven by a ball screw actuator adapted to move the piston at a constant rate. This permits a constant rate of extrusion to be achieved, regardless of a dough's consistency or variations in a dough's consistency. The density of the extrudate will therefore be substantially uniform for the dough being tested.

The cutter assembly, for cutting the extrudate, includes a chain mounted knife blade driven in an endless loop. The knife blade is adapted to cut the extrudate to a predetermined length as it discharges from the annular orifice of the extrusion die. This forms dough pieces of a uniform length and having a uniform wall thickness, which are then cooked to form the snack product test pieces. The knife blade of the cutter assembly is driven through a path which provides an accelerated angular velocity at the point of contact with the extrudate. This insures a precise cut and increases the effectiveness of the knife blade for cutting doughs of various consistencies.

In an illustrative embodiment of the invention, the extrusion die is adapted to form the extrudate into an annular cross sectional shape. The dough pieces cut from the extrudate thus have a ring-like or hollow cylindrical shape. This shape also contributes to the uniformity of the dough pieces. Specifically, the annular orifice of the extrusion die can be situated with respect to the center line of the extrusion piston and inside wall of the extrusion tube to insure a uniform pressure distribution during extrusion and thus a uniform density. Variations in the cooked test pieces, such as expansion or color, can again be attributed to the test ingredients and not the extrusion process.

Various objects, advantages and capabilities of the present invention will become more apparent from the following, more particular description of the preferred embodiments of the invention, as illustrated in the accompanying drawings.

BRIEF DESCRIPTION OF THE DRAWINGS

FIG. 3A is a bottom elevation view of the detachable extrusion tube of the extrusion apparatus;

FIG. 3B is a front elevation view of FIG. 3A;

FIG. 4 is an exploded view showing the assembly of the extrusion tube and extrusion die;

FIG. 5A is an enlarged top view of the extrusion die;

FIG. 5B is an enlarged cross sectional sideview of the extrusion die taken along section line 5B—5B of FIG. 3B;

FIG. 5C is an enlarged bottom view of the extrusion die;

FIG. 6A is a plan view of a snack product test piece formed in accordance with the invention;

FIG. 6B is a side elevation view of FIG. 6A;

DETAILED DESCRIPTION OF THE PREFERRED EMBODIMENT

As used herein the term "extrudate" means extruded dough. The terms "characteristic" and "attribute" refer to features or properties of a dough, test piece or snack product that may be quantified by procedures that are known in the art.

Figure 1:
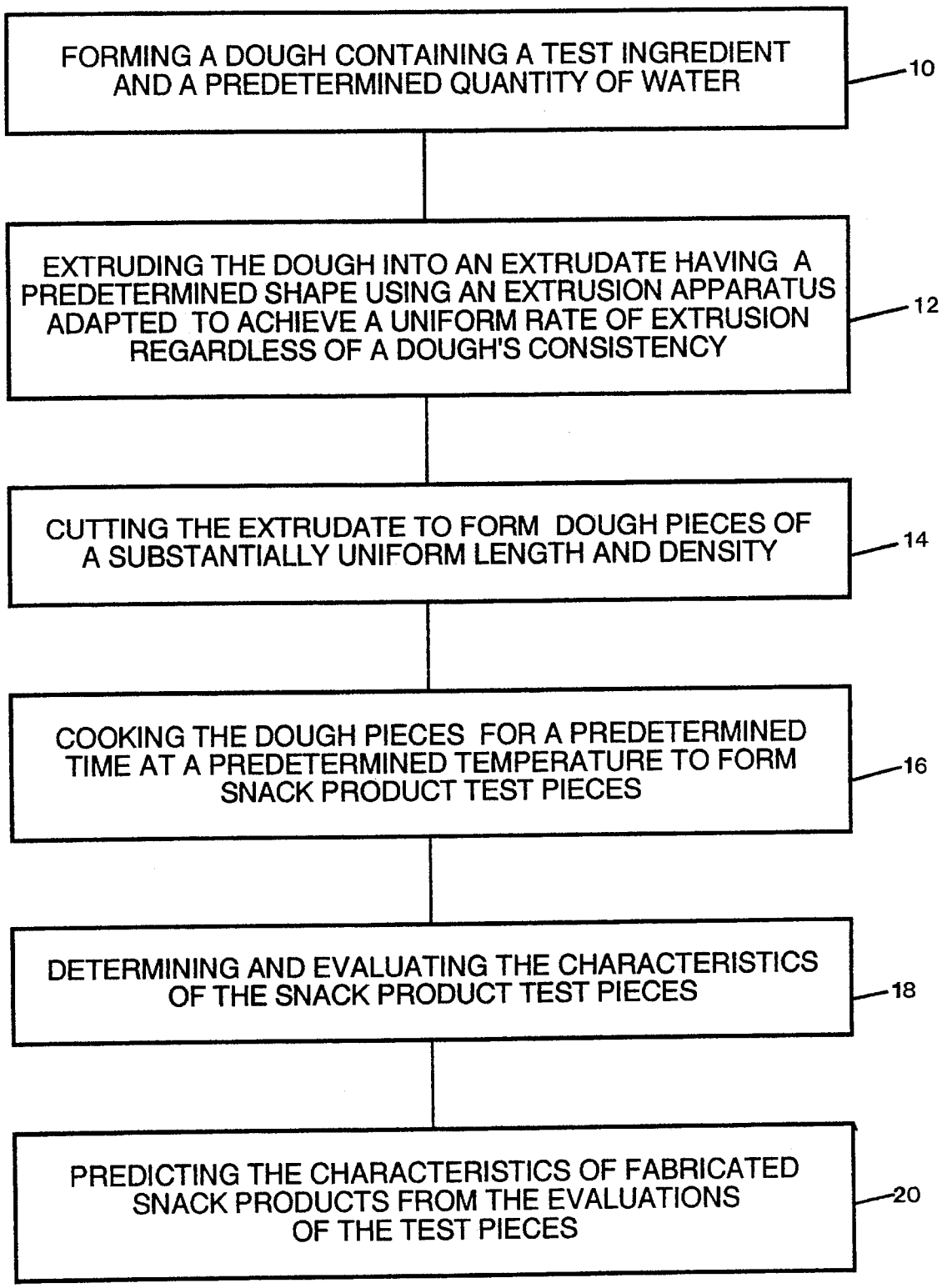
FIG. 1 is a block diagram showing the general steps of the method of the invention.

With reference to FIG. 1, the method of the invention includes the steps of:

forming a dough containing a test ingredient and a predetermined quantity of water; step 10, extruding the dough into an extrudate having a predetermined shape, using an extrusion apparatus adapted to achieve a uniform rate of extrusion regardless of a dough's consistency; step 12, cutting the extrudate to form dough pieces of a substantially uniform length and density; step cooking the dough pieces for a predetermined time at a predetermined temperature to form snack product test pieces; step 16, determining and evaluating the characteristics of the snack product test pieces; step 18, and predicting the characteristics of fabricated snack products from the evaluations of the test pieces, step 20.

Initially a dough is formed, step 10. The dough may be formed in a convenient sized batch using a mixer, food processor or other suitable apparatus. The dough contains at a minimum the test ingredient and water. If a primary snack product ingredient, such as potato flakes, is being evaluated, the dough may be relatively simple containing just the potato flakes under evaluation and a starch ingredient. Alternately the dough ingredients may be a complex formulation of a certain snack product recipe. In this case, the test dough may contain the test ingredient and a number of other necessary ingredients (e.g. potato flakes, corn flour, raw starches, ground dehydrated potatoes, sugar, spices, etc.). The test ingredient may also be a secondary ingredient of a snack product formulation, such as a particular starch under evaluation. In this case, the secondary ingredient can be mixed with a primary ingredient (e.g. potato flakes) of a known quality.

The test ingredient and any other required ingredients are mixed under predetermined conditions. Process parameters such as quantities of water and ingredients, water temperature and mixing time are closely controlled to provide as much uniformity as possible. This allows a meaningful comparison of the snack product test pieces formed with the test ingredient, to a snack product control piece (or control pieces) formed with a control ingredient.

The total quantity of the mixed dough is preferably small, e.g. 454 gm (1 lb.) so that handling is facilitated. In addition, process parameters may be adjusted to achieve a dough having a desired consistency (e.g. Type 2 to Type 9). Following mixing, the dough may be allowed to equilibrate for a predetermined time.

The mixed and equilibrated dough is now ready for extrusion, step 12. Extrusion of the dough is performed using an extrusion apparatus 22 (FIG. 2) constructed in accordance with the invention. A detailed description of the extrusion apparatus 22 will follow. Following extrusion, the dough pieces are cut to form cut dough pieces 36' each having the same length, step 14, The dough pieces 36', are then cooked, step 16, to form snack product test pieces 36. A cooked test piece 36 is shown in FIGS. 6A and 6B. Cooking may be accomplished by frying or baking for a predetermined time at a predetermined temperature.

Next, the characteristics of the test pieces 36 formed with a particular test ingredient may be determined and evaluated, step 18. Different characteristics of the test pieces 36, such as thickness, expansion, color, fat content, bubble distribution, texture, shape, flavor, moisture content, and others may be determined in the laboratory using procedures that quantify or associate some value with the characteristic. Statistical techniques may be used for evaluating the characteristics of a large number of test pieces 36.

Following this determination, an evaluation of the test pieces 36 and thus the test ingredient is performed. A preferred method of evaluation is to compare the test pieces 36 to a control piece (or group of control pieces) fabricated in the same manner with an ingredient comparable to the test ingredient but with known properties. As an example, the test ingredient may comprise a "test" potato flake which is compared to a "normal" potato flake having known properties. In a similar manner, the test ingredient may be a "test" starch which is compared to a "normal" starch having known properties. Evaluation may also be by combining a test ingredient with an ingredient of known quality. As an example, a test ingredient (e.g. starch) may be combined with a "normal" primary ingredient (e.g. potato flake) having known characteristics. Furthermore, evaluation may be a simple assessment of the characteristics of the test pieces 36 and their suitability for a fabricated snack product.

The evaluation process can be used to develop statistical data which may be analyzed using techniques that are known in the art. This information can then be used to predict similar characteristics and their value for fabricated snack products which contain the test ingredients, step 20.

Figure 2:
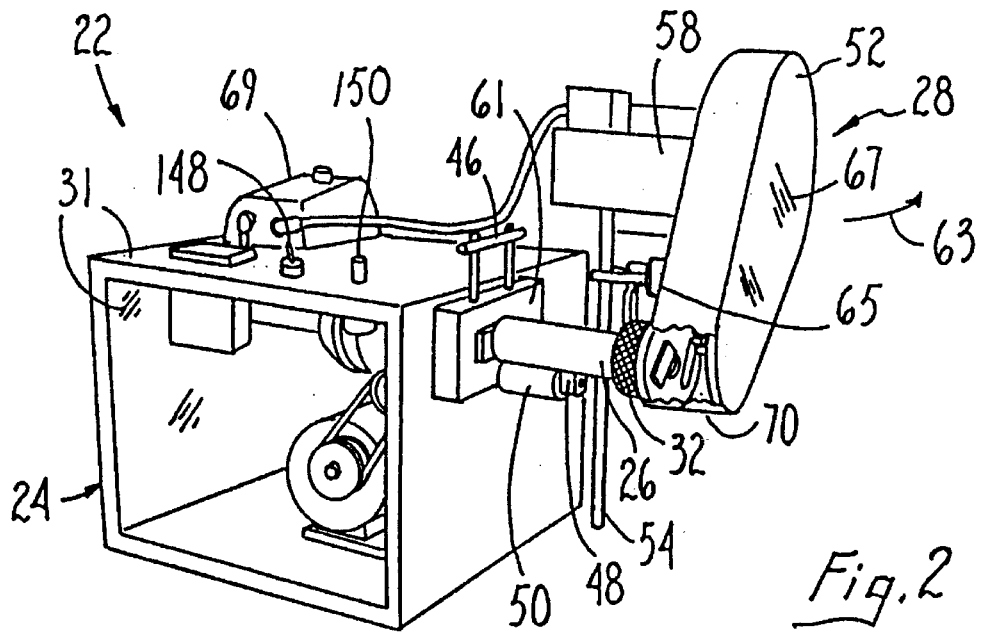
FIG. 2 is a perspective view partially cut away of an extrusion apparatus constructed in accordance with the invention.

Referring now to FIG. 2, the extrusion apparatus 22 is shown. The extrusion apparatus 22 includes: a support frame 24, an extrusion tube 26 detachably mounted to the support frame 24, and a cutter assembly 28 pivotably mounted to the support frame 24.

The extrusion apparatus 22 is adapted to handle dough of different consistencies, from a Type 2 dough to a Type 8 dough. In addition, the extrusion apparatus 22 is adapted to extrude dough at a constant rate regardless of the consistency of the dough and regardless of variations in a dough's consistency. By extruding the dough at a constant rate, the extrudate can be cut by the cutter assembly 28 to a uniform length as it discharges from the extrusion tube 26. The length of the dough pieces will thus always be the same, regardless of a dough's consistency. Moreover, with a constant rate of extrusion, the density of the extrudate will be substantially uniform for a particular dough. Different test ingredients can thus be compared without the introduction of additional variables by the extrusion apparatus 22. This is important because dough pieces with different characteristics, such as length and density, will cook differently. A relatively thick dough piece, for example, will cook slower than a relatively thin dough piece. This may cause the thick dough piece to expand less and the thin dough piece to expand more. In a similar manner a relatively dense dough piece may not expand as much as a relatively porous dough piece.

As shown in FIG. 2, the support frame 24 of the extrusion apparatus 22 is a generally box-like structure formed of metal plates and straps joined to one another by welding or with threaded fasteners. The support frame 24 is enclosed using transparent sheets 31 of a material such as Plexiglas™.

The extrusion tube 26 is detachable from the support frame 24 of the extrusion apparatus 22. This permits the dough that was mixed in step 10, to be loaded by hand (or suitable automated equipment) into the extrusion tube 26. The extrusion tube 26 is shown separately in FIGS. 3A and 3B.

Figure 2A:
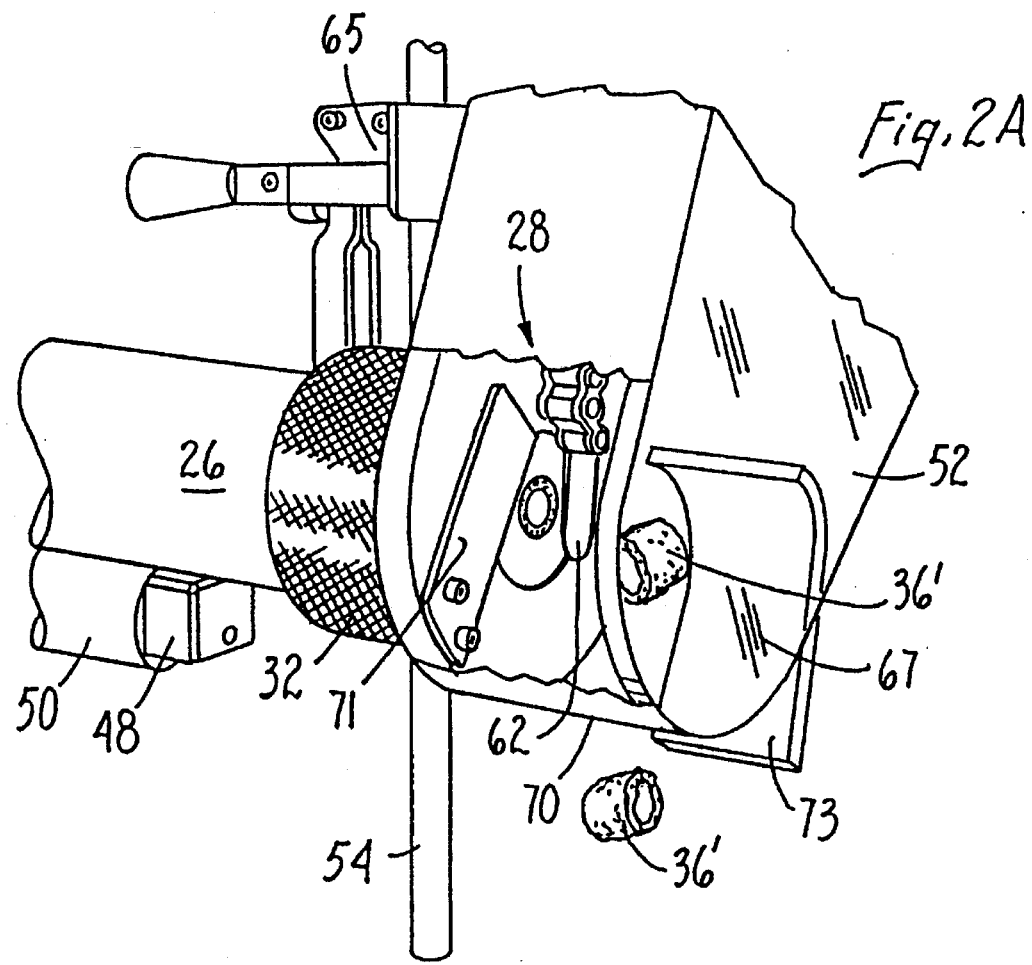
FIG. 2A is an enlarged portion of FIG. 2 and showing the extrusion apparatus in operation.

With reference to FIG. 3A, the extrusion tube 26 is hollow and generally cylindrical in shape. An inlet end 30 of the extrusion tube 26 is open for receiving a quantity of dough. An outlet end 32 of the extrusion tube 26 includes an extrusion die 34. The outlet end 32 of the extrusion tube 26 is detachable and is formed with a knurled surface (FIG. 2A). As shown in FIG. 4, the outlet end 32 of the extrusion tube 26 is held in place by internal threads 29 (FIG. 4) that engage external threads 33 formed on the extrusion tube 26.

The extrusion die 34 is removably attached to an internally threaded opening 35 formed in the outlet end 32 of the extrusion tube 26. The extrusion die 34 includes a die body 37, a tapered post 39, and a post centering ring 41.

The assembled extrusion die 34 is shown in FIGS. 5A, 5B and 5C. As shown in these Figures, the die body 37 is generally cylindrical in shape and has an outside diameter formed with external male threads 47. The external threads 47 mate with the internally threaded opening 35 (FIG. 4) formed in the outlet end 32 of the extrusion tube 26. An outside face 49 (FIG. 5C) of the die body 37 includes openings 51 to facilitate installation and removal of the extrusion die 34 from the outlet end (32) of extrusion tube 26 using a spanner wrench or similar tool. In addition, the die body 37 includes an inside wall 53 (FIG. 5B) that tapers inward from an inlet end to an outlet end thereof.

The tapered post 39 of the extrusion die 34 is shaped substantially as shown in FIG. 5B. The tapered post 39 and the die centering ring 41 are each machined as one piece and are removably attached to one another. When mated, an annular passageway 55 is formed through the die body 37. The annular passageway 55 tapers inwardly from the die centering ring 41 (i.e. inlet end) to the annular orifice 56 (i.e. outlet end). Dough 57 enters the centering ring 41 from the extrusion tube 26 (FIG. 3), passes through the annular passageway 55 and exits through the annular orifice 56.

The die centering ring 41 of the extrusion die 34 is attached to the inlet end of the die body 37. The die centering ring 41 is formed as a plate with an arrangement of openings 59 for channeling the dough 57 into the annular passageway 55 formed through the die body 37. The die centering ring 41, tapered post 39 and annular passageway 55 function to funnel the dough through the annular orifice 56.

The extrudate discharges from the annular orifice 56 as a continuous tube of material. In the preferred embodiment of the invention, the extrudate has a hollow cylindrical shape which is annular in cross section. As will be more fully explained, this shape permits the extrusion die 34 to be located within the extrusion tube 26 to insure the exertion of a uniform pressure on the extrudate.

Referring now to FIG. 3A, the extrusion tube 26 also includes a pair of locking lugs 38, 40 formed with through holes 42, 44. The locking lugs 38, 40 have a generally rectangular peripheral configuration and are adapted for mating engagement with a rectangular shaped slot which is formed on a mounting plate 61 (FIG. 2) of the support frame 24. For securing the extrusion tube 26 to the support frame 24, a c-shaped clamp member 46 (FIG. 2) is passed through openings formed in the mounting plate 61 and placed into the through holes 42, 44 on the mounting lugs 38, 40 of the extrusion tube 26. The extrusion tube 26 also includes a rectangular shaped positioning lug 48 that contacts an abutment block 50 (FIG. 2) on the support frame 24.

Referring back again to FIG. 2, the construction of the cutter assembly 28 will be explained. The cutter assembly 28 functions to cut the extrudate to a predetermined length as it discharges from the extrusion die 34 of the extrusion tube 26. The cutter assembly 28 includes a drive motor 58 and protective enclosure 52. The protective enclosure 52 is pivotably mounted on a pivot post 54 attached to the support frame 24. The protective enclosure 52 can thus be swung into or away from the extrusion tube 26 as indicated by directional arrow 63. A locking mechanism 65 is provided for locking the cutter assembly 28 against the extrusion tube 26.

The protective enclosure 52 of the cutter assembly 28 includes a transparent side 67 formed of a transparent material such as Plexiglas™. The protective enclosure 52 of the cutter assembly 28 also includes a discharge opening 70 and a product deflector 73 which form a chute for the cut dough pieces 36'. The protective enclosure 52 of the cutter assembly 28 is formed with an outer peripheral configuration that matches the drive components for the cutter assembly 28.

Figure 9:
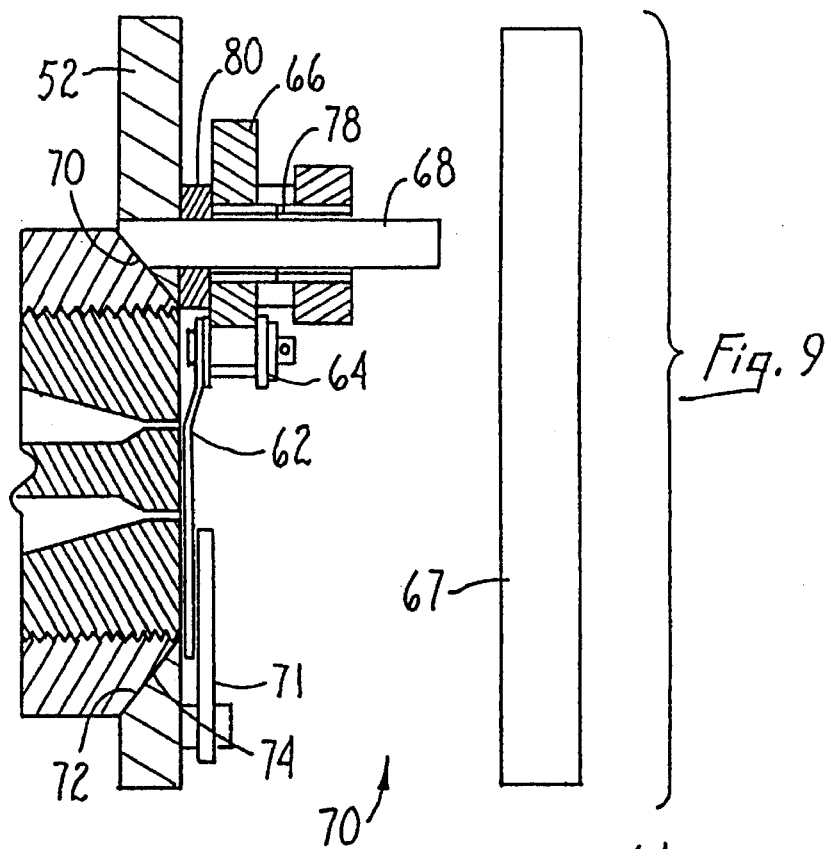
FIG. 9 is an enlarged side elevation view of a portion of the cutter assembly for the extrusion apparatus.
Figure 10:
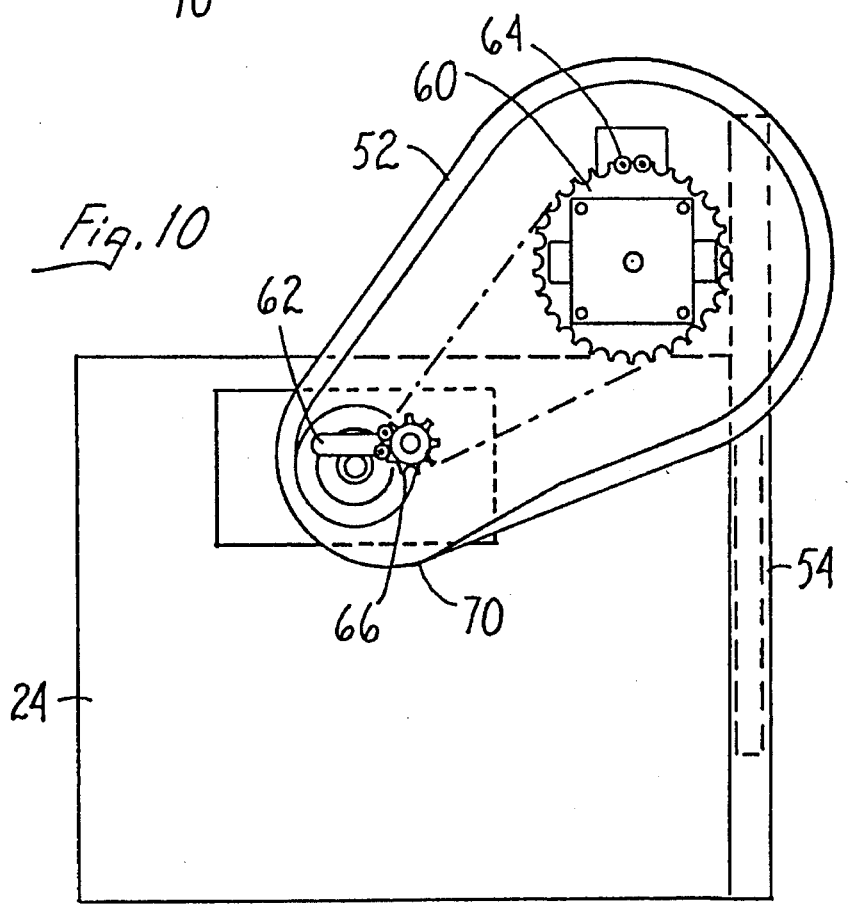
FIG. 10 is a front elevation view of the drive arrangement for the cutter assembly.

Referring now to FIGS. 9 and 10, the cutter drive arrangement is shown. A drive sprocket 60 is attached the output shaft of the cutter drive motor 58. A drive chain 64 is placed in an endless loop around the drive sprocket 60 and around an idler sprocket 66. A knife blade 62 is attached to the drive chain 64. The idler sprocket 66 is freely rotatably mounted on an idler post 68 using caged roller bearings 78. Upon input from the drive motor 58, the drive chain 64 moves the knife blade 62 in a loop around the drive sprocket 60 and idler sprocket 66.

As shown in FIG. 2A, with the cutter assembly 28 placed against the extrusion tube 26, the knife blade 62 is positioned to slide under a spring clip 71 attached to the protective enclosure 52 of the cutter assembly 28 and sever the extrudate discharging from the extrusion die 34. The spring clip 71 supports the extrudate for cutting. One edge of the knife blade 62 may be sharpened to facilitate a clean cut. A spacer 80 (FIG. 9) positions the idler sprocket 66 with respect to the protective enclosure 52. For aligning the protective enclosure 52 with the extrusion tube 26, the protective enclosure 52 includes a countersunk surface 72 (FIG. 9) that mates with a chamfered nose 74 (FIG. 3) of the extrusion tube 26. This arrangement along with the cross sectional shape of the knife blade 62 precisely aligns the path of the knife blade 62 across the discharging extrudate. Cut dough pieces 36' are thus formed and drop by gravity through the discharge opening 70 of the protective enclosure 52.

Since the extrudate discharges from the extrusion die 34 at a constant rate and the rpms of the knife blade 62 are constant, a length of the cut dough pieces 36' is the same for each dough piece 36. This length can be adjusted, however, by varying the rpms of the knife blade 62. In this regard, the cutter drive motor 58 is a variable speed motor 58 which allows the speed of the knife blade 62 to be varied. The cutter drive motor 58 is connected to a DC drive controller 69 mounted on the top of the support frame 24 for the extrusion apparatus 22. A representative range of rpm's for the knife blade 62 is about 600 rpm to 1800 rpm. A suitable cutter drive motor 58 is sold by Dayton as Model No. 47528.

One feature of the cutter assembly 28 is that the knife blade 62 is adapted to accelerate through the extrudate. As clearly shown in FIG. 11, the idler sprocket 66 has a smaller outside diameter than the drive sprocket 60. As the knife blade 62 moves around the smaller idler sprocket 66, its angular velocity ($\omega$) increases because of the well known relationship ($v=r\omega$), as r becomes smaller. This permits an accelerated angular velocity for the knife blade 62 at the point of contact of the knife blade 62 with the extrudate.

If a hot oil fryer is used to cook the dough pieces 36', the fryer may be placed under the cutter assembly 28 such that the cut dough pieces 36' will drop through the opening 70 in the protective enclosure 52 and into the hot oil. Alternately the cut dough pieces 36' may be otherwise collected for cooking to form the cooked test pieces 36. As shown in FIGS. 6A and 6B, each cooked test piece 36 is ring-like in shape and has an inside diameter (ID), an outside diameter (OD), a length (L) and a wall thickness (T).

Figure 7:
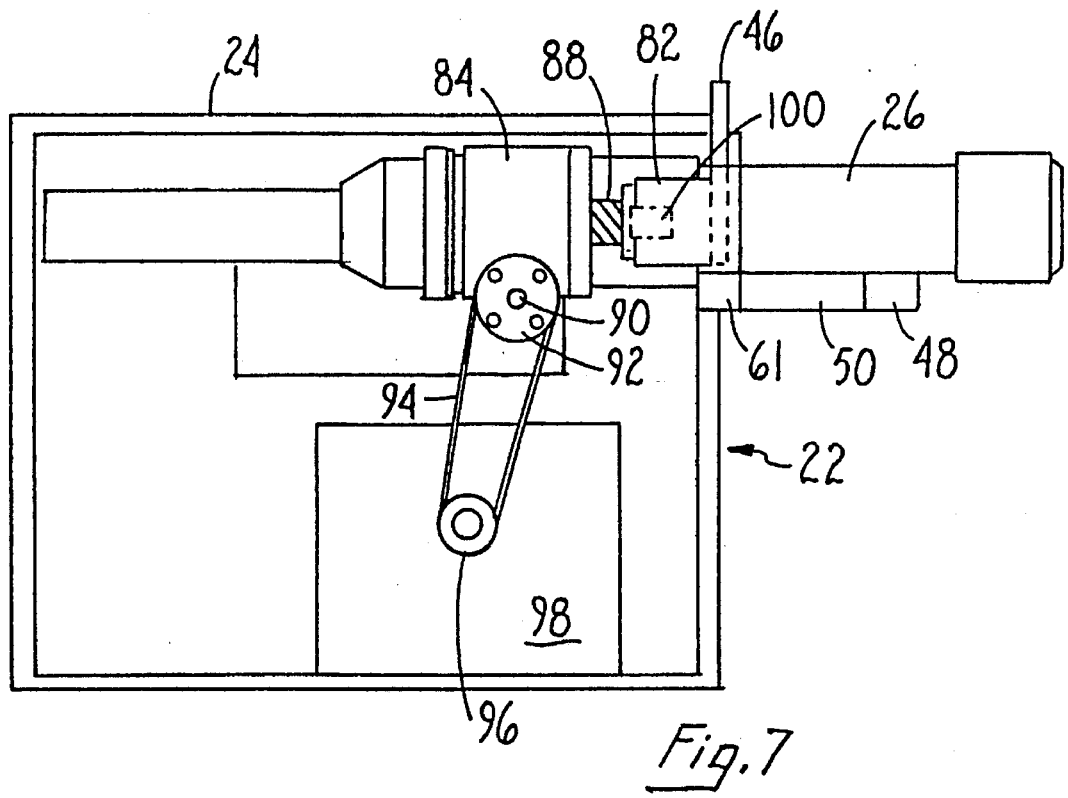
FIG. 7 is a side elevation view of the extrusion apparatus with the cutter assembly removed.
Figure 8:
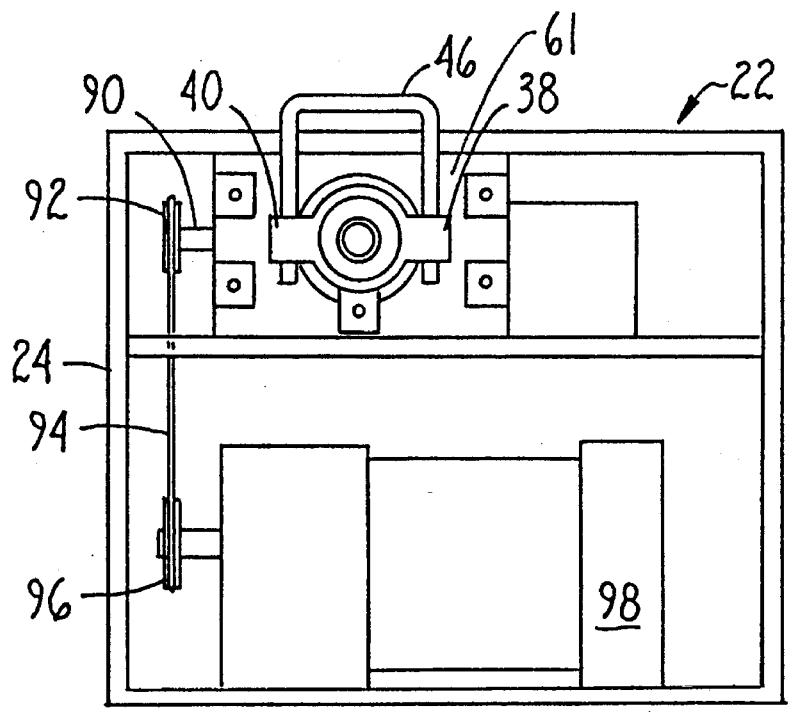
FIG. 8 is a front elevation view of the extrusion apparatus with the cutter assembly removed.

Referring now to FIGS. 7 and 8, the construction of the extrusion apparatus 22 is shown in more detail. In these Figures the extrusion apparatus 22 is shown separate from the cutter assembly 28. The main components of the extrusion apparatus are: the support frame 24; the extrusion tube 26; an extrusion piston 82 for pushing the dough 57 through the extrusion tube 26; and a ball screw actuator 84 for driving the extrusion piston 82.

The support frame 24 and the extrusion tube 26 have been described previously. The extrusion piston 82 is mounted for movement within the extrusion tube 26 by the ball screw actuator 84. The extrusion piston 82 is generally cylindrical in shape. The outside diameter of the extrusion piston 82 is slightly less than the inside diameter of the extrusion tube 26. The extrusion piston 82 may be formed of a material such as hard plastic which will move easily through the extrusion tube 26 without sticking or galling the inner cylindrical wall of the extrusion tube 26. The extrusion piston 82 is attached to a translating screw 88 of the ball screw actuator 84. For effecting this attachment, the translating screw 88 has a threaded end 100 that is screwed into mating internal threads formed on the extrusion piston 82.

One feature of the extrusion apparatus 22 is that the extrusion piston 82 is adapted to be moved in a linear direction at a uniform rate. The ball screw actuator 84 is adapted to move the translating screw 88 and thus the extrusion piston 82 in a linear direction at a uniform rate. The ball screw actuator 84 is attached to the support frame 24 with the longitudinal axis of the translating screw 88 in alignment with the longitudinal axis of the extrusion tube 26. The direction of motion of the extrusion piston 82 is along a longitudinal axis of the extrusion tube 26. A suitable ball screw actuator 84 may be purchased from Duff-Norton and is designated as a "2800 And 9800 Series Ball Screw Actuator Unit". The desired configuration is as a "Translating Screw (Inverted)". This type of ball screw actuator is also described in U.S. Pat. No. 3,178,958 which is incorporated herein by reference.

In general, this type of ball screw actuator 84 is adapted to convert torque from a drive motor to a precise linear movement of the translating screw 88. The ball screw actuator 84 includes an internal nut (not shown) that is fixed to a rotating gear (not shown). The rotating gear meshes with a worm gear (not shown) connected to an input shaft 90. Rotation of the input shaft 90 moves the translating screw 88 forward or backward as required. The translating screw 88 moves linearly but does not turn. The ball screw actuator 84 also includes a brake (not shown) for stopping the movement of the translating screw 88.

The input shaft 90 of the ball screw actuator 84 is attached to a sheave 92. A drive sheave 96 is attached to the output shaft of an extruder drive motor 98. A drive belt 94 drivably connects the drive sheave 96 with the sheave 92 in the input shaft 90.

The drive motor 98 for the ball screw actuator 84 is a reversible motor. A suitable drive motor 98 is sold by Dayton as Model No. 2Z851. By appropriately selecting the rotational speed of the drive motor 98, a desired linear speed of the translating screw 88 can be achieved. This linear speed will be constant regardless of the load that is generated as the dough is pushed through the extrusion die 34 of the extrusion tube 26. A uniform rate of extrusion can thus be maintained regardless of a dough's consistency, and the density of the cut dough pieces for a dough will be uniform.

Figure 12:
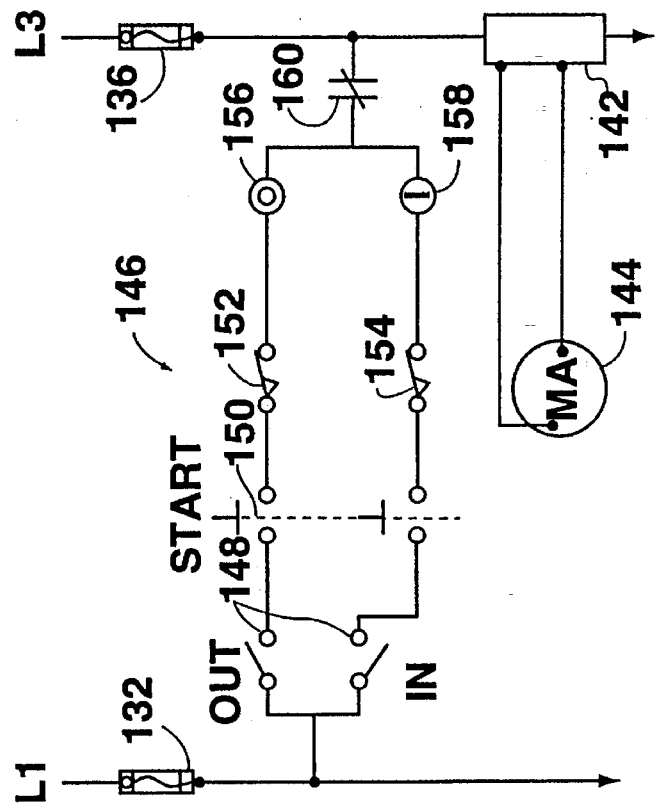
FIG. 12 is an electrical schematic showing a control circuit for the drive motor.
Figure 11:
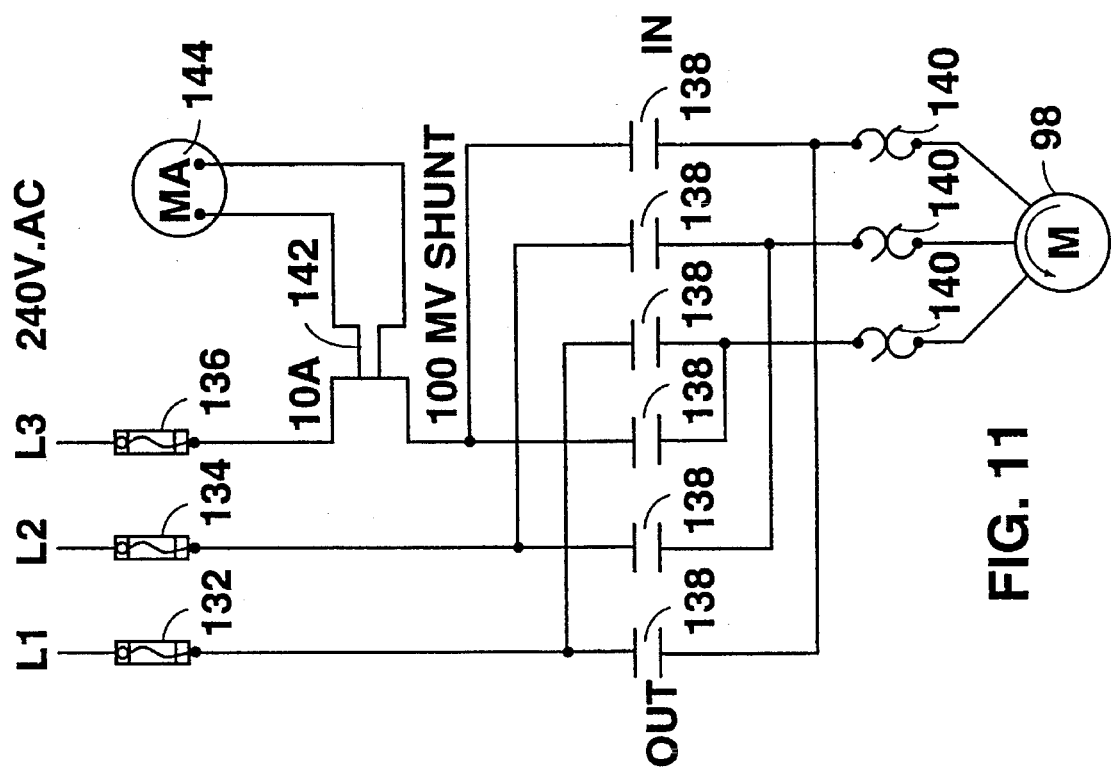
FIG. 11 is an electrical schematic showing a wiring arrangement for a drive motor of the extrusion apparatus.

Referring now to FIGS. 11 and 12, wiring and control arrangements for the drive motor 98 of the ball screw actuator 84 are shown. As shown in FIG. 11, the drive motor 98 is a three phase 240 V AC motor. Three supply lines L1, L2, and L3 for the drive motor 98 are wired with fuses 132, 134, 136. The supply lines L1, L2, L3 are wired to relays contacts 138 and 140 and to the drive motor 98 substantially as shown. A 10A 100 MV shunt 142 is connected to one of the supply lines L3. The shunt 142 in turn is wired to a milliammeter 144. The milliammeter 144 can be used to monitor the amperage being drawn by the drive motor 98 as an indicator of the extrusion pressure generated during the extrusion process.

FIG. 12 shows a suitable control circuit 146 for the drive motor 98. The control circuit 146 includes a directional switch 148 that determines the direction of rotation of the drive motor 98 and thus the movement of the extrusion piston 82 as "in" or "out". A manually depressable operational switch 150 must be depressed to enable the drive motor 98. In addition, the control circuit 146 includes auxiliary contacts 152, 154 and relays 156, 158 that function as limit switches for limiting the "in" and "out" movement of the extrusion piston 82. Contacts 152, 154 may be physically located on the extrusion piston 82 and extrusion tube 26 using techniques that are known in the art. Another contact 160 functions as a final limit switch.

Figure 13:
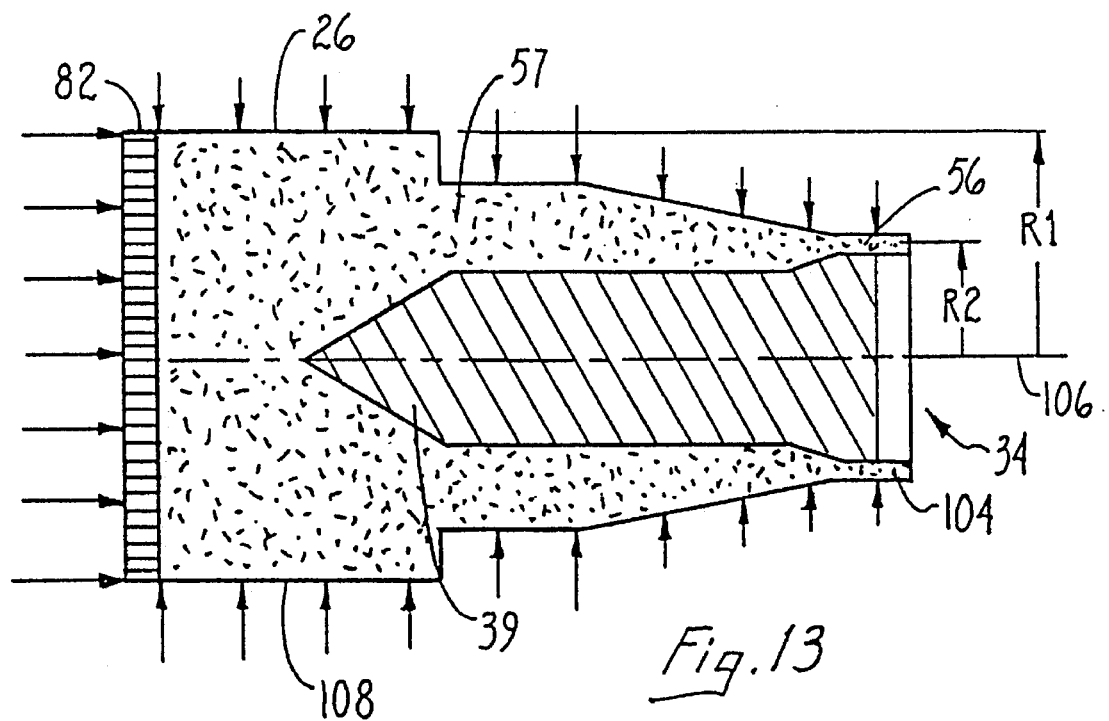
FIG. 13 is a schematic representation of the extrusion piston and extrusion tube showing the extrusion die and its placement in the extrusion tube for achieving a uniform pressure distribution.

Referring now to FIG. 13, a schematic representation of the extrusion piston 82, extrusion die 34 and annular orifice 56 are shown. This view is intended to illustrate the optimal placement of the annular orifice 56 of the extrusion die 34 with respect to the inside wall 108 of the extrusion tube 26. In FIG. 13, the dough 57 in the extrusion tube 26 is being compressed by the extrusion piston 82 as it is forced through the annular orifice 56 of the extrusion die 34. The extrusion tube 26 includes a cylindrical inside wall 108 and a longitudinal axis 106. The extrudate 104 discharges as a hollow cylinder having an annular cross section.

As the extrusion piston 82 pushes on the dough 57, pressure is exerted in a horizontal direction as indicated by the horizontal arrows at the interface of the dough 57 with extrusion piston 82. Pressure is also exerted in a vertical direction as indicated by the vertical arrows where the dough 57 contacts the inside wall 108 of the extrusion tube 26. In the center of the dough 57, however, along the longitudinal axis 106 of the extrusion tube 26, there is relatively less vertical pressure than at the circumferential edges of the dough 57. The dough 57 at the center is therefore not as compressed and is less dense. The point of equilibrium, where the vertical pressure forces are equalized is half way between the longitudinal axis 106 and the inside wall 108 of the extrusion tube 26. By locating the annular orifice 56 of the die 34 exactly midway between the longitudinal axis 106 and the inside wall 108, an absolutely uniform pressure is exerted on the dough being extruded. The extrudate 104 for the dough 51 will therefore discharge with a uniform density.

In FIG. 13, R1 represents the distance from the longitudinal axis 106 of the extrusion tube 26 to the inside wall 108 of the extrusion tube 26. R2 represents the distance between the longitudinal axis 106 and the midpoint of the annular orifice 56 of the extrusion die 34. The relationship between R1 and R2 for achieving a uniform extrusion pressure is $R2 = R1/2$.

Figure 14:
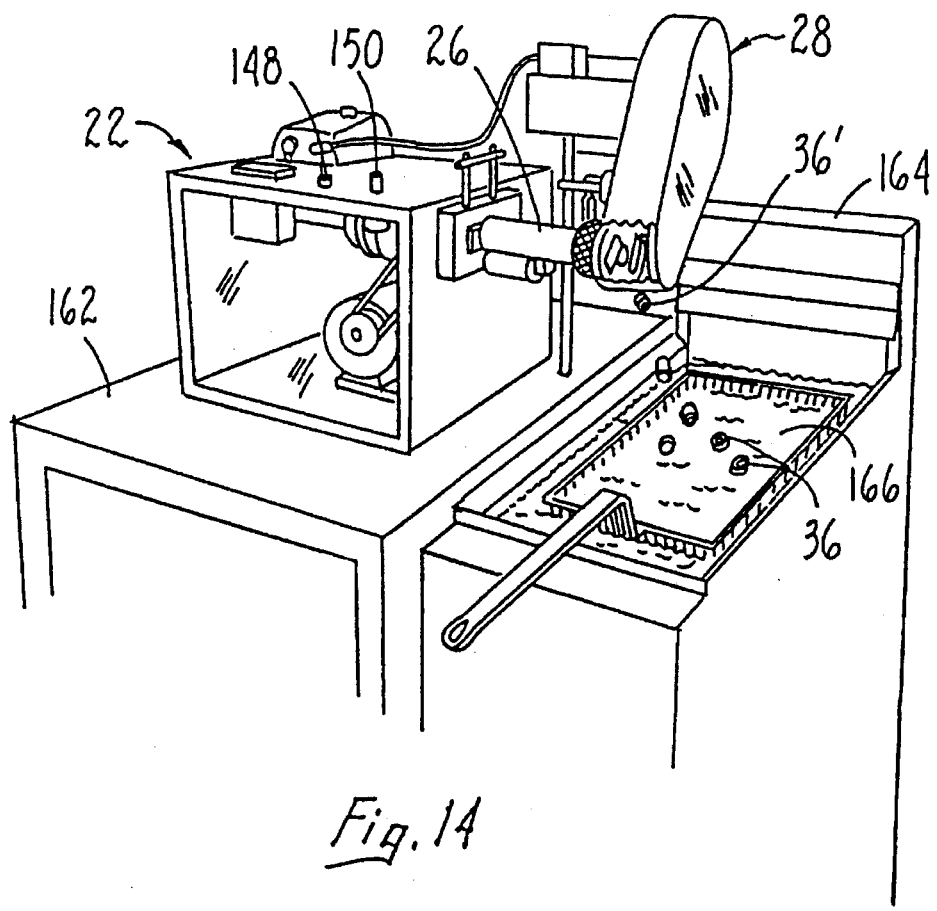
FIG. 14 is a perspective view partially cut away of the extrusion apparatus and a fryer set up for testing snack product ingredients in accordance with the invention.

Referring now to FIG. 14, a laboratory set up for the extrusion apparatus 22 is shown. The extrusion apparatus is supported on a table 162. A fryer 164 filled with hot oil 166 is placed beside the table 162. The fryer 164 is situated such that the cut dough pieces 36' drop into the hot cooking oil 166. Prior to extrusion of the dough pieces 36' the extrusion tube 26 is removed and loaded with a predetermined quantity of dough.

LABORATORY PROCEDURE

The following representative test procedure uses the method and apparatus of the invention. This procedure illustrates testing potato flakes for use in a fabricated potato snack product. The following test formulation was used for evaluating the potato flakes:

| A. Formulation | |
| --- | --- |
| Batch size: | 454 gm |
| Raw potato starch: | 40.6% |
| Potato flakes: | 57.9% |
| Flour salt: | 1.5% |
| Water, to achieve | 45% dough moisture |

The formulation and dough moisture are varied to produce a workable test dough and a test product consistently shaped from the ingredient being tested. If, for example, potato granules are being tested instead of potato flakes, the test formula may require a higher percentage of granules and less water, as granules have a lower water absorption capacity. If the ingredients being tested are raw starches, an increased level of starch may be useful in evaluating the characteristics of the different starches. Complex formulations which contain more ingredients than shown here can also be tested once the optimum formula for making the test dough has been determined.

In all tests, duplicate samples are made of each test ingredient and the results are averaged.

B. Equipment

The basic test procedure utilizes the following equipment:

1. Dough mixer: A Cuisinart food processor with mixing blade, KitchenAid or Hobart paddle mixer, or other similar mixers can be used. Because of different mixer designs and configurations, it is essential that the same mixer be used for producing the control and test samples.

2. Water addition: A calibrated burette positioned over the mixing bowl is preferred. Water can also be poured carefully from a beaker over a timed period.
3. Extrusion Apparatus 22.
4. Temperature-controlled batch fryer—Frymaster Model H14 or equivalent.

C. Dough Preparation The 454 gm batch of dough is prepared as follows:

1. Weigh potato starch, potato flakes and flour salt.
2. Place weighed ingredients in the mixer and mix for 10 seconds.
3. Place the required 60° F. (15.6° C.) water into the burette or a 250 ml beaker.
4. Turn mixer on and add water over a 15 second period.
5a. (For Cuisinart) Continue mixing for a total of seconds. Remove dough from the mixing bowl into a small bowl, break up any lumps, then return to the Cuisinart mixing bowl. Mix for 5 additional seconds.
5b. (For KitchenAid or Hobart mixer) Mix for a total of 2 minutes on speed #2.
6. Let dough sit in mixing bowl, covered, for 10 minutes.

D. Extrusion, Cutting and Cooking Procedure

Preheat fryer oil to 345° F. (174° C.) and maintain throughout testing.

The extrusion apparatus 22 is positioned with the cutter assembly 28 located over the center of the fryer 164 substantially as shown in FIG. 14, enabling the dough pieces 36 to drop by gravity into the fryer 164 as they are cut by the cutter assembly 28.

Assemble the extrusion type 26 components. A 1.18 mm ring extrusion die 34 with a beveled ring behind the annular orifice 56 is used for these tests.

Form half of the dough into a cylindrical shape and place the formed dough into the extrusion tube 26. Tamp the dough lightly into the extrusion tube 26 and repeat until the tube is filled to about 2 inches from the top.

Insert the extrusion tube 26 into the support frame 24 of the extrusion apparatus 22 and place the clamp member 46 through the extrusion tube 26 and mounting plate 86 of the support frame 22 to hold the extrusion tube 26 in place. Swing the cutter assembly 28 forward and lock it in place in front of the extrusion die 34. Set speed of cutter drive motor 58 to achieve desired length for the cut dough pieces 36, normally 10.5 mm (±0.5 mm).

Turn directional switch 148 for the extruder drive motor 98 to the right (forward direction). Turn on the cutter drive motor 58 at the beginning of the extrusion and turn off when dough is extruded. Hold down operational switch 150 and continue to hold down until all dough is extruded out of the extrusion tube 26.

Begin stirring heated oil 166 with spatula (not shown) as dough pieces emerge from cutter. A timer is started when the first dough piece 36' drops into the fryer 164. The total fry time is typically 2.5 minutes. Continue to stir uniformly to keep dough pieces 36' separate as they fry.

Amperage readings from the extruder drive motor 98 are read approximately 10 seconds after extrusion of product begins.

At end of frying, the basket is removed from the fryer 164 and fried test pieces 36 are placed on paper towels and allowed to cool.

Turn directional switch 148 on extruder drive motor 98 to the left (reverse direction) and hold down operational switch 150 until extrusion piston 82 is returned to original position and extruder drive motor 98 stops.

Cutter assembly 22 is unlocked from the front of the extrusion tube 26 and swung back.

C-shape lock member 46, holding extrusion tube 26 in place is removed.

Remove and clean extrusion tube 26, extrusion die 34 and annular orifice 56 before next test.

E. Evaluation of Test Results

1. Dough evaluations

Moisture: Dough sample is ground and moisture determined with a CEM AVC 80.

Dough type. Rated on a scale of 1–9 as referenced above.

2. Fried Product

Color: Determined using an Agtron colorimeter.

Moisture content: Fried samples are ground and moisture determined with a Sartorious moisture balance.

Length: Two measurements per ring are made using calipers. Longest and shortest sides are measured and results averaged. Ten rings of each sample are measured.

Fat content: Determined using a rapid method with a hexane extraction.

Thickness and expansion ratio: Break ring into two pieces so longest and shortest cut off areas are at the break. Measure thickness of broken edge at the center point of each side. Repeat for ten rings and average results.

3. Other Process Measurements

Fry temperature: Temperature at which fryer stabilizes during frying of rings, normally 345° F. (174° C.).

Fry time: Time which elapses from when first dough piece falls into fryer until cooked dough piece is removed from the fryer, typically 2.5 minutes.

Extruder amperage: Amperage required to operate the ball screw actuator 84 which pushes the piston 82 which extrudes the dough. Reading is taken ten seconds after extrusion begins.

The preferred method of evaluation of the fried test pieces 36 is by comparison to control pieces formed in the same manner using an ingredient having known characteristics or properties. Once a sufficient data base has been developed, this evaluation process can be performed rapidly by laboratory and plant technicians. In addition, the procedure may be used for evaluating different formula ingredients. Such evaluations may be made by simply assessing the organoleptic characteristics of the fried test pieces.

Fry times can be varied depending on the objective of the test. If the objective is to determine the differences between the water absorptive capacity of various flakes, the pieces are fried for a predetermined time and analyzed for residual moisture. If the objective is to determine differences in the color of the final fried product, samples containing the different flakes would be fried to an established moisture content, normally about 2.0%.

EXAMPLE 1

In these examples the term bench top extruder (BTE) is used for the extrusion apparatus 22 previously described. A sample comprises a batch of dough formed with a test ingredient.

Two representative samples were selected from each of seven separate lots of low-leach/low peel (LL/LP) potato flakes made by a single manufacturer under varied test conditions. There were thus a total of fourteen samples. These fourteen samples were formed into separate batches of dough and then extruded and cut in accordance with the method and apparatus of the invention to form test pieces substantially as previously described. The expansion ratio, Agtron color, and fat content (%) of these test pieces were then determined and assigned a value.

As expected, the results of the tests of the different samples varied according to the different process conditions used in making the flake products. However, the close agreement between the duplicate samples confirmed that uniform test pieces could be made using the method and apparatus of the invention.

Table 1A shows the analytical data for the 14 samples. The Expansion Ratio, Agtron Color, and Fat Content of each test piece was evaluated.

TABLE 1A

EVALUATED CHARACTERISTICS

| Sample # | EXPANSION RATIO | | AGTRON COLOR | | FAT CONTENT (%) | |
|---|---|---|---|---|---|---|
| | Test #1 | Test #2 | Test #1 | Test #2 | Test #1 | Test #2 |
| 602.01-15B | 3.5 | 3.7 | 50 | 58 | 20.8 | 20.9 |
| 602.01-15C | 4.1 | 3.9 | 49 | 46 | 18.4 | 19.7 |
| 602.01-15D | 4.5 | 4.6 | 85 | 83 | 21.1 | 21.6 |
| 602.01-15E | 3.9 | 4 | 75 | 77 | 21.1 | 21.9 |
| 602.01-15F | 4.3 | 4.1 | 72 | 77 | 21.1 | 22 |
| 602.01-15G | 4.3 | 4.2 | 75 | 78 | 22.1 | 22.1 |
| 602.01-15H | 4.3 | 4.1 | 84 | 83 | 21.6 | 21.6 |

Table 1B shows the results of an Analysis of Variance of the data from Table 1A. This analysis indicates little, if any, difference between duplicate samples from the same lots, but significant differences among samples from the different lots.

TABLE 1B

ANALYSIS OF VARIANCE

| CHARACTERISTIC TESTED | SIGNIFICANCE OF DIFFERENCE BETWEEN DUPLICATE SAMPLES | SIGNIFICANCE OF DIFFERENCE BETWEEN DIFFERENT SAMPLES |
|---|---|---|
| Expansion Ratio | No Significance | 99% |
| Agtron Color | No Significance | 99% |
| Fat Content | 95% | 99% |
| Piece Count | No Significance | 95% |

EXAMPLE 2

A quantity of LL/LP flakes with relatively low reducing sugar content (i.e. 0.78%) was used to prepare a series of ten 453.5 gm dough samples with increasing sugar content. Sufficient dextrose was added to each flake sample and mixed intimately with the potato particles to increase the reducing sugar content incrementally between 0.78% to 2.8%. Duplicates of each flake sample were also mixed with water and tested for a total of twenty samples.

Dough batches made from the samples were extruded and cut using the bench top extruder (BTE) (i.e. extrusion apparatus 22) substantially as previously described. Each test piece formed from the samples was fried for 150 seconds at 345° F. (174° C.) and the color measured in an Agtron colorimeter. The results for the two samples of each test dough were averaged as shown in Table 2.

TABLE 2

EFFECT OF REDUCING SUGAR CONTENT ON AGTRON COLOR

| REDUCING SUGAR (%) | AGTRON COLOR |
|---|---|
| 0.78 | 65.00 |
| 0.99 | 59.00 |
| 1.22 | 56.00 |
| 1.44 | 50.00 |
| 1.67 | 48.50 |
| 1.90 | 46.00 |
| 2.13 | 42.00 |
| 2.35 | 42.00 |
| 2.59 | 40.00 |
| 2.82 | 39.50 |

Figure 15:
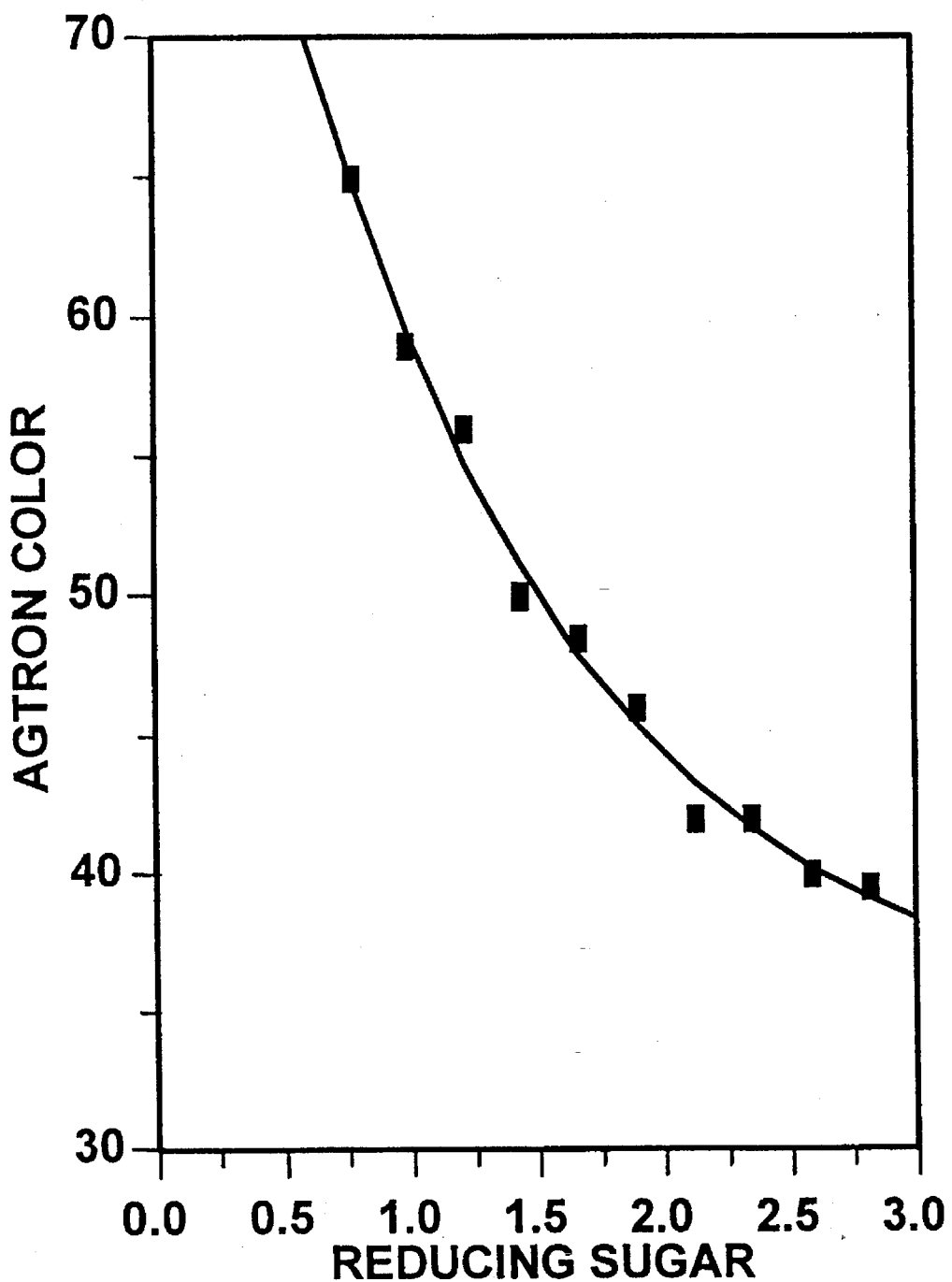
FIG. 15 is a graph plotting Agtron color vs. reducing sugar content for test samples as outlined in example 2.

FIG. 15 shows a graph of the regression curve of Agtron color vs reducing sugar content for the ten test samples. The correlation coefficient for reducing sugar with Agtron color was determined to be 0.992. This demonstrates that the Agtron color is highly significantly affected by reducing sugar level and thus can be used in the BTE test to predict the reducing sugar level in test samples of ingredients.

EXAMPLE 3

A pilot plant test was designed to confirm that the expansion of test pieces fabricated in accordance with the invention with a test potato ingredient, could be used to predict the expansion of a sheeted potato snack made from the same ingredient. A series of thirteen different samples of LL/LP potato flakes, obtained from a number of suppliers, were used to make cooked test pieces in accordance with the method and apparatus previously described. Critical characteristics of the test pieces such as the expansion ratio, Agtron color, moisture content, dough type, fat content and motor amperage during extrusion were evaluated. This data was utilized to predict the characteristics of a sheeted fabricated snack food product that contained the same potato flakes.

For comparison, sheeted rippled snacks were made according to the process described in Example 1 of U.S. Pat. No. 4,973,481, incorporated herein by reference. This patent is the basis for the Ripplins™ brand potato snacks manufactured by the Keebler Company. Critical characteristics of the rippled snacks (i.e. "Ripplins") such as thickness and Agtron color, were determined.

A comparison was then made between the BTE-predicted characteristics and the actual measured characteristics of the fabricated rippled snacks. Table 3A lists the expansion ratio, Agtron color, and free starch content, as measured by the prior art method described in U.S. Pat. No. 3,998,975 to Liepa, in order of increasing expansion for BTE test pieces made in accordance with the invention. Regression analysis of the measured values with the expansion ratio was made and correlation coefficients ($R^2$) were determined.

TABLE 3A

BTE TEST DATA

| RUN # | LOG # | POTATO FLAKE FREE STARCH (%) | EXPANSION RATIO | AGTRON |
|---|---|---|---|---|
| 602.01-16C | 6747 | 32.7 | 3.4 | 39 |
| 602.01-16D | 6748 | 31.2 | 3.4 | 39 |
| 601.01-13A | 6535 | 24.8 | 3.5 | 46 |
| 602.01-15B | 6750 | 27.9 | 3.6 | 54 |
| 602.01-16A | 6757 | 32.2 | 3.6 | 47 |
| 602.01-15A | 6749 | 28.4 | 3.9 | 79 |
| 602.01-15C | 6751 | 35.7 | 4.0 | 48 |
| 602.01-15E | 6753 | 40.4 | 4.0 | 76 |
| 602.01-13A | 6700 | 31.5 | 4.1 | 63 |
| 602.01-15F | 6754 | 42.7 | 4.2 | 75 |
| 602.01-15H | 6756 | 32.8 | 4.2 | 84 |
| 602.01-15G | 6755 | 41.6 | 4.3 | 77 |
| 602.01-15D | 6752 | 40.9 | 4.6 | 84 |

Table 3B lists the results of similar measurements made on the Ripplins snack products produced as outlined above from the same thirteen samples of LL/LP potato flakes.

TABLE 3B

RIPPLINS ™ TEST DATA

| RUN # | LOG # | POTATO FLAKE FREE STARCH (%) | THICKNESS (mm) | AGTRON |
|---|---|---|---|---|
| 970.11-35B | 6747 | 32.7 | 1.29 | 62 |
| 970.11-35C | 6748 | 31.2 | 1.22 | 61 |
| 970.11-34B | 6535 | 24.8 | 1.33 | 61 |
| 970.11-34D | 6750 | 27.9 | 1.39 | 56 |
| 970.11-35A | 6757 | 32.2 | 1.29 | 64 |
| 970.11-34C | 6749 | 28.4 | 1.40 | 72 |
| 970.11-34E | 6751 | 35.7 | 1.50 | 60 |
| 970.11-34G | 6753 | 40.4 | 1.55 | 74 |
| 970.11-34A | 6700 | 31.5 | 1.54 | 71 |
| 970.11-34H | 6754 | 42.7 | 1.49 | 71 |
| 970.11-34K | 6756 | 32.8 | 1.48 | 77 |
| 970.11-34J | 6755 | 41.6 | 1.54 | 74 |
| 970.11-34F | 6752 | 40.9 | 1.49 | 78 |

Figure 16:
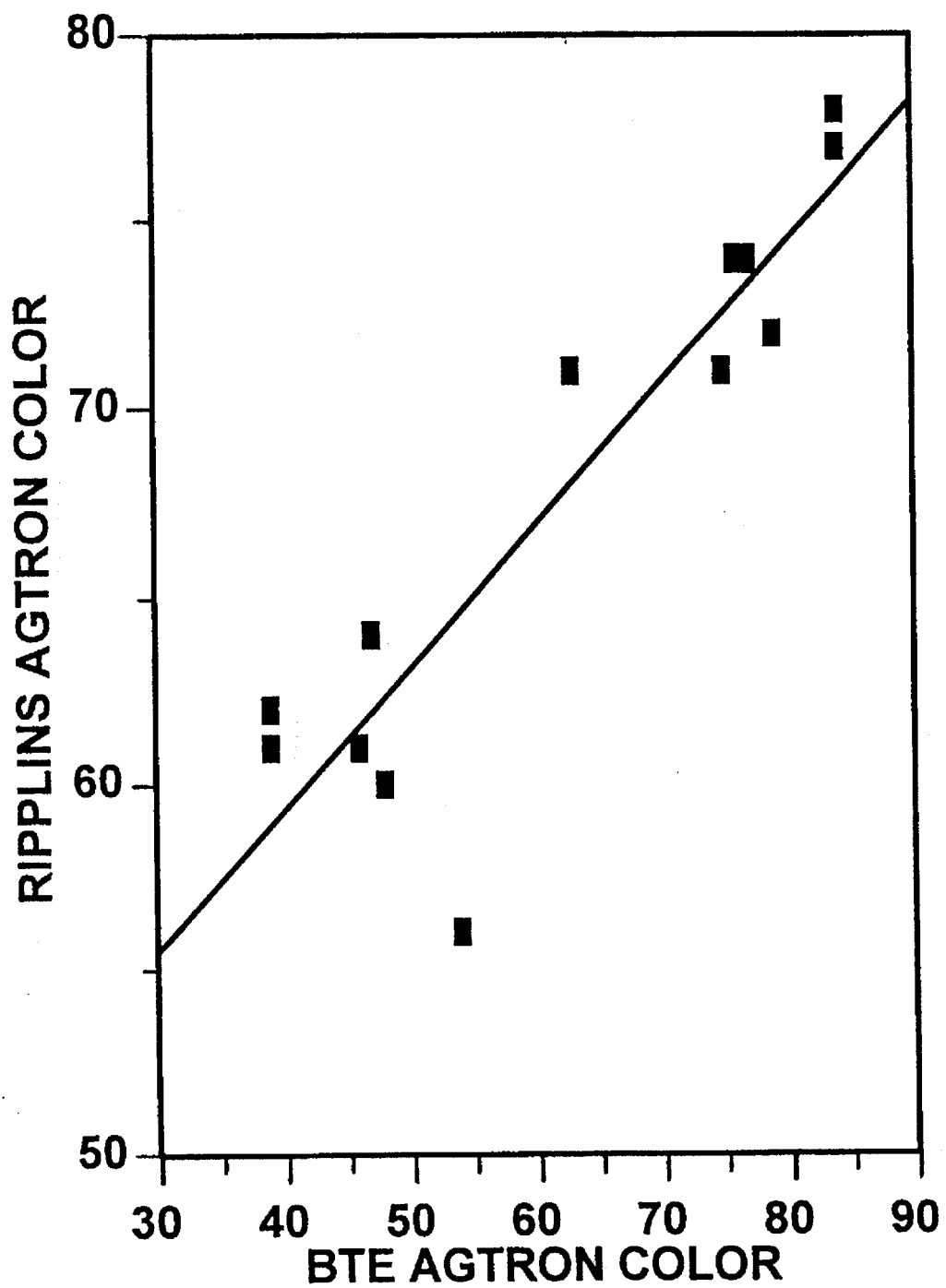
FIG. 16 is a graph plotting Agtron color of rippled potato snacks (Ripplins™) fabricated as outlined in example 3 vs. the Agtron color for test samples formed in accordance with the invention.
Figure 17:
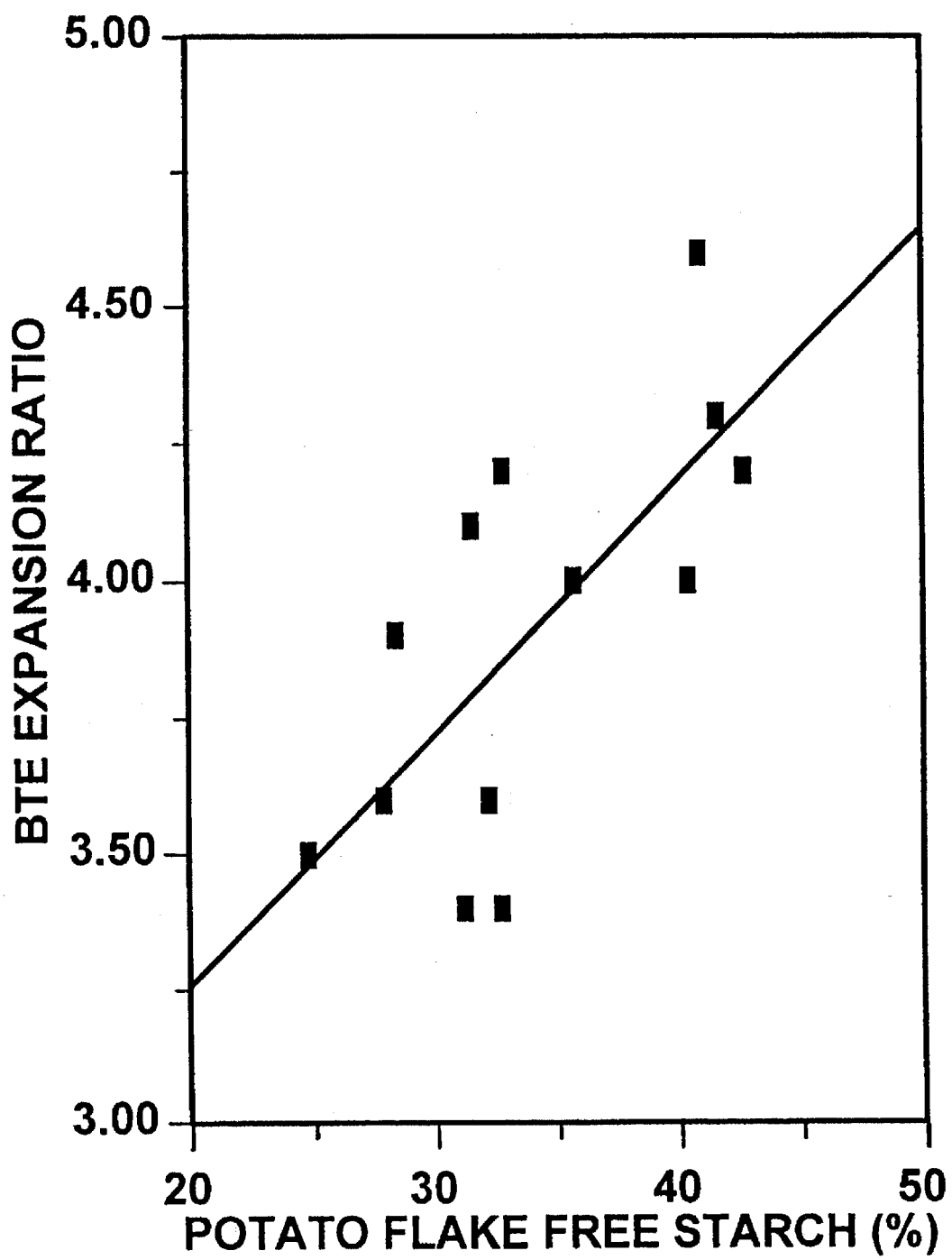
FIG. 17 is a graph plotting the expansion ratio of samples formed in accordance with the invention vs. potato flake free starch as outlined in Example 3.
Figure 18:
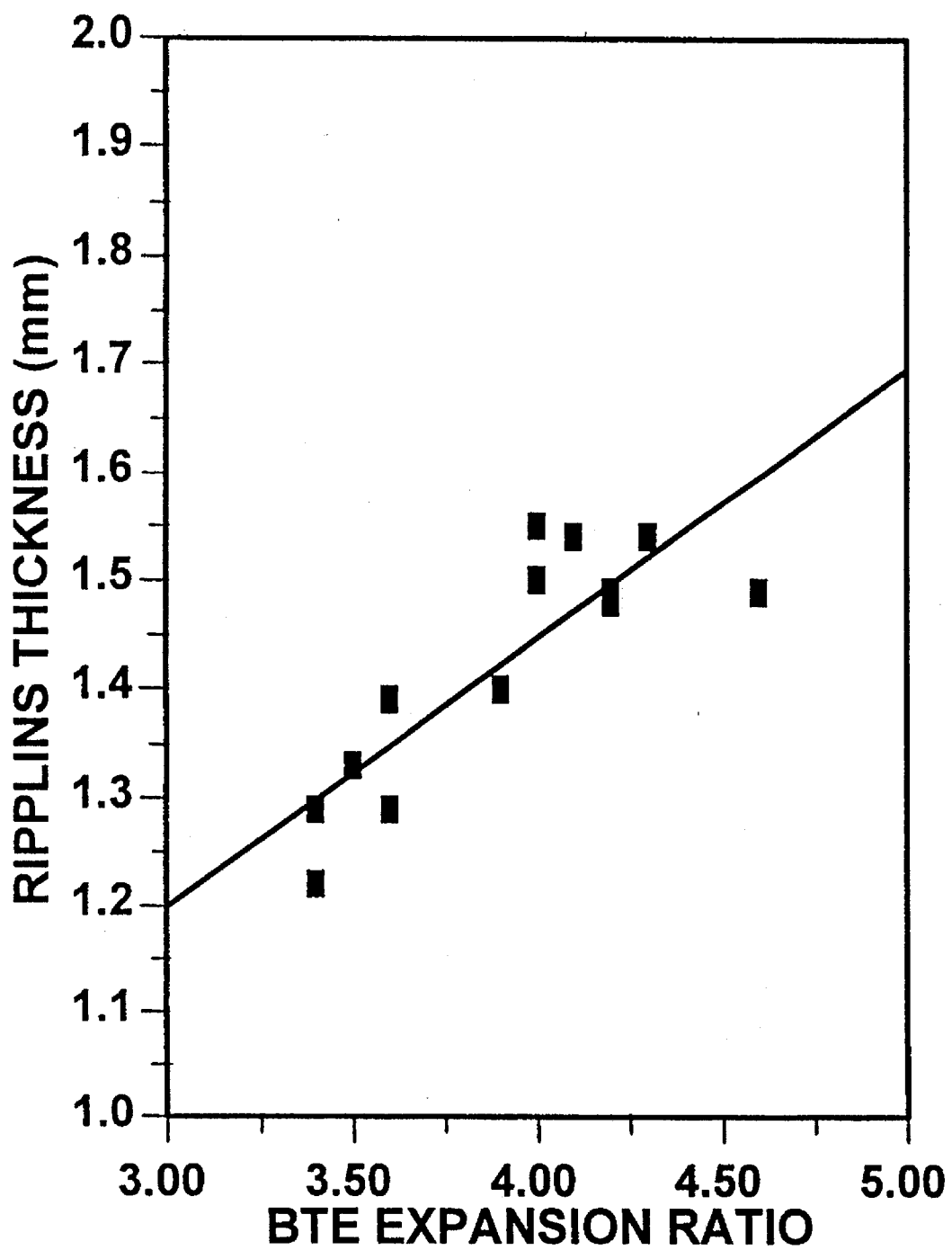
FIG. 18 is a graph plotting the thickness of rippled potato snacks (Ripplins™) vs. the expansion ratio of samples formed in accordance with the invention.

FIGS. 16 to 18 show regression plots demonstrating the successful application of the invention in the tests of Example 3, as follows.

FIG. 16 shows a regression plot of Ripplins Agtron Color vs. BTE Agtron color for the thirteen samples. A high correlation coefficient (R2) of 0,813 was determined and demonstrates that the color of the test pieces accurately predicted the color of the fabricated snack.

FIG. 17 shows a regression plot of the BTE Expansion Ratio for the flake samples compared with the flake free starch as determined by the Liepa method. A correlation coefficient (R2) of only 0.498 was determined, thus demonstrating the inability of the free starch test to predict the BTE Expansion Ratio.

FIG. 18 shows a regression plot of the Ripplins thickness vs. BTE Expansion Ratios. A correlation coefficient (R2) of 0.719 was calculated as outlined above.

Figure 19:
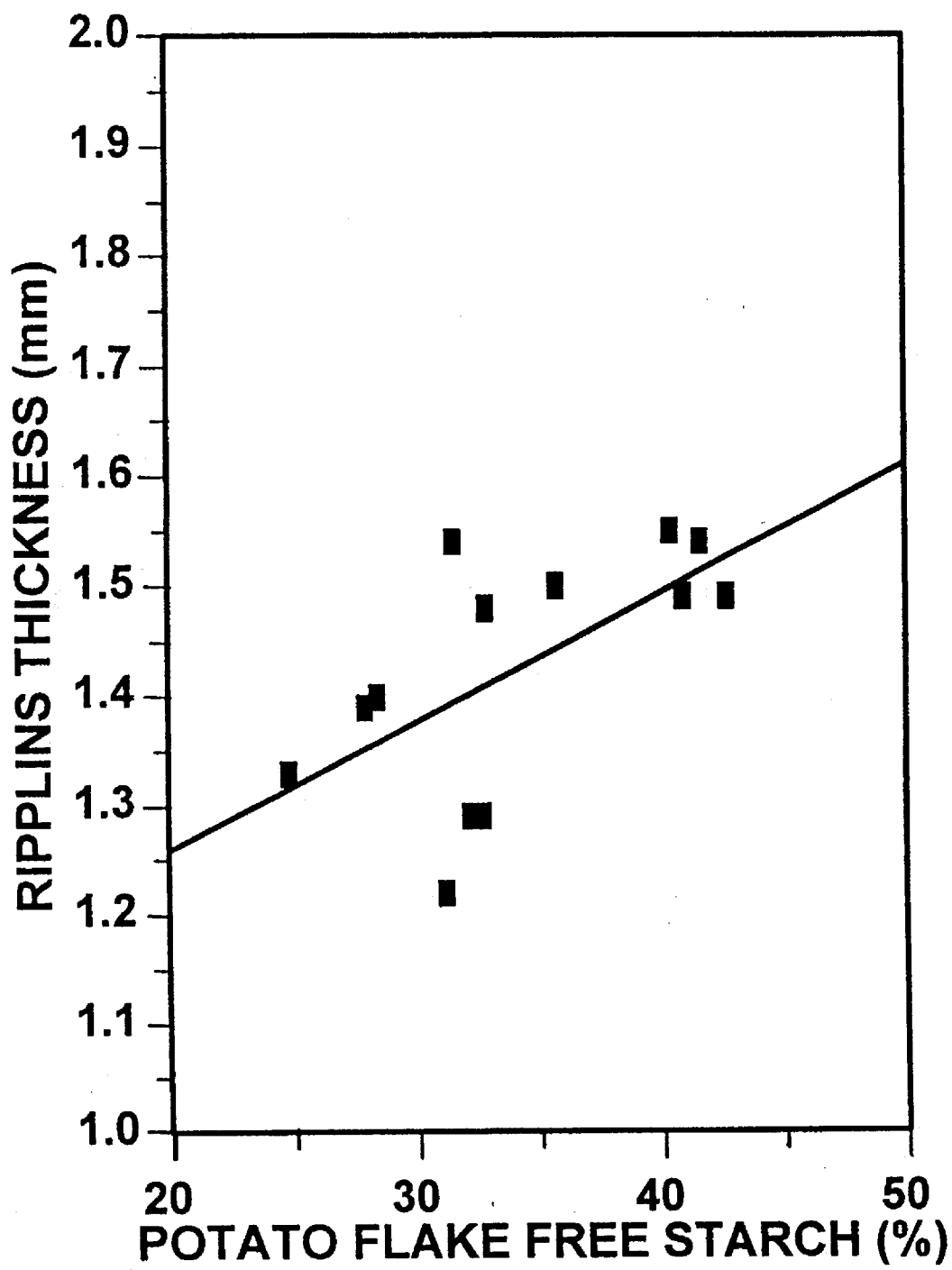
FIG. 19 is a graph plotting the thickness of samples made in accordance with the prior art test procedure outlined in U.S. Pat. No. 4,973,481 (Ripplins™) vs. the starch content analysis of potato samples.

FIG. 19 shows a regression plot of the Ripplins thickness vs. potato flake free starch. FIG. 19 illustrates a further weakness of the prior art method disclosed in the above cited Liepa patent. A correlation coefficient (R2) of only 0.370 was determined between the free starch and the Ripplins thickness. This is significantly less than the correlation of 0.719 shown in FIG. 18 for the BTE Expansion ratios obtained in accordance with the invention. Thus it can be concluded that the present invention provides improved and unexpected results since correlation coefficients for predicted characteristics are much higher than with prior art procedures.

While the method and apparatus of the invention have been described with reference to certain preferred embodiments, as will be apparent to those skilled in the art, certain changes and modifications can be made without departing from the scope of the invention as defined by the following claims.

What is claimed is:

1. A method for testing an ingredient for a fabricated snack product, comprising the steps of:

forming a dough containing a test ingredient and a predetermined quantity of water under predetermined mixing conditions;

extruding the dough into a predetermined shape at a uniform rate by using an extruding apparatus having a ball screw actuator and motor means for driving the ball screw actuator to provide an extrudate having a uniform density;

cutting the extrudate to form dough pieces each having a same length;

cooking the dough pieces at a predetermined temperature for a predetermined time to form snack product test pieces;

determining and evaluating at least one characteristic of the test pieces; and predicting for a fabricated snack product containing the test ingredient a characteristic similar to one evaluated in the test pieces.

2. The method as recited in claim 1 and wherein evaluation is by analyzing certain characteristics of the test pieces by procedures suitable for identifying desirable snack product characteristics including color, expansion and fat content.

3. The method as recited in claim 1 and wherein the test ingredient is combined with a primary ingredient of known quality.

4. The method as recited in claim 1 and wherein the snack product test pieces are formed as cylindrical rings.

5. The method as recited in claim 1 and wherein the snack product test pieces are cooked by deep fat frying.

6. A method for predicting characteristics of a fabricated snack product containing a test ingredient, comprising the steps of:

forming a dough containing the test ingredient and a predetermined quantity of water under predetermined mixing conditions;

extruding the dough through an orifice in an extruding apparatus having ball screw actuator and motor means for driving the ball screw actuator whereby the dough is extruded at a uniform rate of extrusion regardless of dough consistency to form an extrudate having a predetermined shape and a uniform density;

cutting the extrudate into dough pieces each having a same length;

cooking the dough pieces at a predetermined temperature for a predetermined time to form snack product test pieces;

evaluating the test pieces by determining and analyzing characteristics of the test pieces using procedures suitable for identifying snack product characteristics; and predicting similar characteristics of the fabricated snack product using information obtained during the evaluating step.

7. The method as claimed in claim 6 wherein the evaluating step further comprises comparing the test pieces to fabricated snack product pieces made using an ingredient having known properties.

8. The method as claimed in claim 6 and wherein the dough contains the test ingredient as a primary ingredient and water.

9. The method as claimed in claim 6 and wherein the test ingredient is selected from the class of ingredients consisting of potato flakes, potato granules, potato starches, and ground dehydrated potatoes.

10. The method as claimed in claim 6 and wherein a composition of the dough replicates a snack food recipe.

11. The method as claimed in claim 6 and wherein the dough contains a starch as a test ingredient and a primary ingredient of known quality.

12. The method as claimed in claim 6 and wherein a determined characteristics of the test pieces is selected from the group of characteristics consisting of color, expansion, texture, shape and fat content.

13. The method as claimed in claim 6 and wherein the orifice is annular.

14. The method as claimed in claim 6 and wherein the dough pieces are cylindrically shaped.

15. The method as claimed in claim 6 and wherein the fabricated snack product is a sheeted product.

16. The method as claimed in claim 6 and wherein the predicted similar characteristics of the fabricated snack product include thickness, color, and fat content.

17. A method for predicting characteristics of a fabricated snack product containing a test ingredient, comprising the steps of:

forming a dough containing the test ingredient and a predetermined quantity of water under predetermined mixing conditions;

extruding the dough to form an extrudate having a predetermined shape and a uniform density using an extrusion apparatus adapted to extrude the dough at a uniform rate regardless of a consistency of the dough, said extrusion apparatus comprising a ball screw actuator and a constant speed drive motor;

cutting the extrudate into dough pieces of a same length;

frying the dough pieces in hot oil at a predetermined temperature for a predetermined time to form snack product test pieces;

evaluating the test pieces by determining and analyzing one or more characteristics of the test pieces using procedures suitable for identifying snack product characteristics; and predicting a similar characteristic and its value for the fabricated snack product containing the test ingredient using information obtained during the evaluating step.

18. The method as claimed in claim 17 and wherein the extrusion apparatus comprises:

an extrusion tube having an inlet end for receiving a quantity of the dough and an outlet end having an extrusion die formed with an orifice;

piston means reciprocally mounted within the extrusion tube for pushing the dough through the orifice of the extrusion die;

said ball screw actuator and constant speed drive motor for moving the piston means at a constant rate regardless of a consistency of the dough; and cutter means for cutting the dough pieces to a uniform length as the extrudate discharges from the orifice of the extrusion die.

19. The method as claimed in claim 18 and wherein the cutter means includes a cutter knife which has an accelerated angular velocity as it cuts the extrudate.

20. The method as claimed in claim 18 and wherein the extrusion die orifice is an annular orifice which is located midway between a longitudinal axis of the extrusion tube and an inside wall of the extrusion tube to provide a uniform pressure distribution across the annular orifice.

21. The method as claimed in claim 18 and wherein frying is accomplished with a fryer placed under the extrusion apparatus to receive dough pieces discharged from the extrusion die.

* * * * *